US009504521B2

(12) United States Patent
Deutmeyer et al.

(10) Patent No.: US 9,504,521 B2
(45) Date of Patent: Nov. 29, 2016

(54) SURGICAL TOOL ARRANGEMENT

(75) Inventors: Kurt M. Deutmeyer, San Jose, CA (US); Braden M. Robison, Fremont, CA (US); Andrew J. Hamel, San Mateo, CA (US); Michael G. Hilldoerfer, Mountain View, CA (US)

(73) Assignee: STRYKER CORPORATION, Kalamazoo, MI (US)

( * ) Notice: Subject to any disclaimer, the term of this patent is extended or adjusted under 35 U.S.C. 154(b) by 1502 days.

(21) Appl. No.: 11/886,393

(22) PCT Filed: Mar. 17, 2006

(86) PCT No.: PCT/US2006/009802
§ 371 (c)(1),
(2), (4) Date: Sep. 14, 2007

(87) PCT Pub. No.: WO2006/102124
PCT Pub. Date: Sep. 28, 2006

(65) Prior Publication Data
US 2008/0188848 A1   Aug. 7, 2008

Related U.S. Application Data

(60) Provisional application No. 60/662,735, filed on Mar. 17, 2005.

(51) Int. Cl.
*A61B 18/14*   (2006.01)
*A61B 17/32*   (2006.01)
(Continued)

(52) U.S. Cl.
CPC ..... *A61B 18/1485* (2013.01); *A61B 17/32002* (2013.01); *A61B 17/32* (2013.01); *A61B 18/14* (2013.01); *A61B 2017/0046* (2013.01); *A61B 2018/00178* (2013.01)

(58) Field of Classification Search
CPC .......... A61B 2018/00202; A61B 2018/00208; A61B 2018/00601; A61B 2018/00607; A61B 2018/00916; A61B 2018/00946; A61B 18/148; A61B 18/1482; A61B 17/320758; A61B 17/320783; A61B 17/32002

USPC .................................................... 606/32–50
See application file for complete search history.

(56) References Cited

U.S. PATENT DOCUMENTS 1,814,791 A   7/1931   Ende
1,952,617 A   3/1934   Wappler
(Continued)

FOREIGN PATENT DOCUMENTS

CN   1130052 A   9/1996
CN   1655728 A   8/2005
(Continued)

OTHER PUBLICATIONS

Trident° The Power of Three, webpage from http://www.conmed.com/products, ConMed Linvatec-Arthroscopy—ESA—Trident™ (2001).
(Continued)

*Primary Examiner* — Ronald Hupczey, Jr.
(74) *Attorney, Agent, or Firm* — Flynn, Thiel, Boutell & Tanis, P.C.

(57) ABSTRACT

A surgical tool arrangement including a powered handpiece which cooperates with a combined electrosurgical and mechanical cutting instrument. The electrosurgical and mechanical cutting instrument includes an outer static housing element which defines an electrode for delivering electrical energy to the surgical site, and a cutting element disposed within the outer housing and movable relative thereto for manipulating patient tissue. The electrosurgical and mechanical cutting instrument is an integral component attachable to the surgical tool to provide multiple functions in a single instrument, such as cauterization, ablation and mechanical cutting, without the need for attachment of additional housing structures or other adapters. The tool arrangement also includes a universal handpiece which is capable of accepting and operating a number of different surgical instruments, each having one or multiple functions.

21 Claims, 18 Drawing Sheets

(51) Int. Cl.
*A61B 17/00* (2006.01)
*A61B 18/00* (2006.01)

(56) References Cited

U.S. PATENT DOCUMENTS

| | | | |
|---|---|---|---|
| 2,056,377 | A | 10/1936 | Wappler |
| 2,275,167 | A | 3/1942 | Bierman |
| 3,746,814 | A | 7/1973 | Lackey et al. |
| 3,945,375 | A | 3/1976 | Banko |
| 4,034,761 | A | 7/1977 | Prater et al. |
| 4,232,676 | A | 11/1980 | Herczog |
| 4,301,802 | A | 11/1981 | Poler |
| 4,700,997 | A | 10/1987 | Strand |
| 4,815,462 | A * | 3/1989 | Clark ............... 606/170 |
| 4,850,354 | A * | 7/1989 | McGurk-Burleson et al. ............... 606/170 |
| 4,998,527 | A | 3/1991 | Meyer |
| 5,084,045 | A | 1/1992 | Helenowski |
| 5,192,292 | A | 3/1993 | Cezana et al. |
| 5,217,478 | A | 6/1993 | Rexroth |
| 5,217,479 | A * | 6/1993 | Shuler ............... 606/180 |
| 5,254,117 | A | 10/1993 | Rigby et al. |
| 5,277,696 | A | 1/1994 | Hagen |
| 5,364,395 | A | 11/1994 | West, Jr. |
| 5,413,575 | A | 5/1995 | Haenggi |
| 5,429,596 | A | 7/1995 | Arias et al. |
| 5,492,527 | A | 2/1996 | Glowa et al. |
| 5,527,331 | A | 6/1996 | Kresch et al. |
| 5,607,391 | A | 3/1997 | Klinger et al. |
| 5,609,573 | A | 3/1997 | Sandock |
| 5,782,795 | A * | 7/1998 | Bays ............... 604/22 |
| 5,810,809 | A * | 9/1998 | Rydell ............... 606/49 |
| 5,827,279 | A | 10/1998 | Hughett et al. |
| 5,860,975 | A | 1/1999 | Goble et al. |
| 5,904,681 | A * | 5/1999 | West, Jr. ............... 606/41 |
| 5,925,045 | A | 7/1999 | Reimels et al. |
| 5,941,876 | A | 8/1999 | Nardella et al. |
| 6,004,320 | A | 12/1999 | Casscells et al. |
| 6,007,533 | A | 12/1999 | Casscells et al. |
| 6,149,646 | A | 11/2000 | West, Jr. et al. |
| 6,193,715 | B1 * | 2/2001 | Wrublewski et al. ......... 606/45 |
| 6,214,001 | B1 * | 4/2001 | Casscells et al. ............ 606/41 |
| 6,312,441 | B1 | 11/2001 | Deng |
| 6,464,512 | B2 | 10/2002 | Morita |
| 6,485,436 | B1 | 11/2002 | Truckai et al. |
| 6,610,059 | B1 | 8/2003 | West, Jr. |
| 6,663,628 | B2 * | 12/2003 | Peters ............... 606/45 |
| 6,692,516 | B2 | 2/2004 | West, Jr. et al. |
| 6,827,725 | B2 | 12/2004 | Batchelor et al. |
| 6,837,888 | B2 | 1/2005 | Ciarrocca et al. |
| 6,840,937 | B2 | 1/2005 | Van Wyk |
| 6,918,906 | B2 | 7/2005 | Long |
| 6,979,332 | B2 * | 12/2005 | Adams ............... 606/45 |
| 7,052,494 | B2 | 5/2006 | Goble et al. |
| 7,060,063 | B2 | 6/2006 | Marion et al. |
| 7,150,747 | B1 * | 12/2006 | McDonald et al. ............ 606/45 |
| 7,226,460 | B2 * | 6/2007 | Gibson et al. ............... 606/180 |
| 7,452,358 | B2 | 11/2008 | Stern et al. |
| 7,682,333 | B2 | 3/2010 | Deng |
| 7,887,559 | B2 | 2/2011 | Deng et al. |
| 7,918,852 | B2 | 4/2011 | Tullis et al. |
| 2003/0060862 | A1 | 3/2003 | Goble et al. |
| 2004/0078037 | A1 | 4/2004 | Batchelor et al. |
| 2005/0080412 | A1 | 4/2005 | Ouchi |
| 2005/0107779 | A1 | 5/2005 | Ellman et al. |
| 2005/0228374 | A1 | 10/2005 | Desinger et al. |
| 2006/0200123 | A1 | 9/2006 | Ryan |
| 2006/0235377 | A1 | 10/2006 | Earley et al. |
| 2006/0264927 | A1 | 11/2006 | Ryan |
| 2007/0016185 | A1 | 1/2007 | Tullis et al. |
| 2008/0058802 | A1 | 3/2008 | Couture et al. |
| 2009/0299366 | A1 | 12/2009 | Desinger et al. |
| 2009/0306656 | A1 | 12/2009 | Desinger et al. |
| 2011/0301578 | A1 | 12/2011 | Muniz-Medina et al. |

FOREIGN PATENT DOCUMENTS

| | | |
|---|---|---|
| CN | 1780588 A | 5/2006 |
| CN | 2868225 Y | 2/2007 |
| CN | 102333490 A | 1/2012 |
| DE | 196 41 564 C1 | 10/1996 |
| JP | 03143437 A2 | 6/1991 |
| JP | 2005-536272 A | 12/2005 |
| JP | 2008-532712 A | 8/2008 |
| WO | WO 85/00280 | 1/1985 |
| WO | WO 90/07303 | 7/1990 |
| WO | WO 97/24073 A1 | 7/1997 |
| WO | WO 97/33523 | 9/1997 |
| WO | WO 98/03117 | 1/1998 |
| WO | WO 99/13788 | 3/1999 |
| WO | WO 2004/017849 A1 | 3/2004 |
| WO | WO 2006/102124 A2 | 9/2006 |
| WO | WO 2010/098809 A3 | 9/2010 |

OTHER PUBLICATIONS

ConMed's Linvatec Subsidiary Announces the Release of the Trident(TM) Resection Ablator, 2 pages, Apr. 19-22, 2001.
Smith & Nephew, Dyonics Electroblade, webpage from http://global.smith-nephew.com (2005).
Coagulating Arthroscopy Shaver: A New Device, Vahan A. Kilaghbian, M.D., (7 pages) (1996).
International Preliminary Report on Patentability from corresponding PCT application mailed Sep. 27, 2007 (13 pages).
International Search Report and Written Opinion-from corresponding PCT application mailed Nov. 10, 2006 (20 pages).
Office Action of Japanese Patent Office dated Sep. 13, 2013 with English translation issued in Japanese Application No. 2011-552019 (7 pages).
European Office Action issued in Appln. No. 06738812.4 dated Dec. 23, 2010 (4 pages).
Japanese Office Action issued in Appln. No. 2008-502112 dated Aug. 22, 2011 with English Translation (7 pages).
Japanese Office Action issued in Appln. No. 2008-502112 dated Feb. 20, 2012 with English Translation (7 pages).
Australian Examination Report Issued in Appln. No. 2010218473 dated Jan. 23, 2013 (4 pages).
European Office Action issued in Appln. No. 06738812.4 dated Feb. 1, 2013 (3 pages).
Chinese Office Action issued in Appln. No. 201080009460.0 dated May 27, 2013 with English Translation (11 pages).
Australian Examination Report issued in Appln. No. 2010218473 dated Jun. 3, 2013 (3 pages).
European Office Action issued in Appln. No. 06738812.4 dated May 6, 2014 (3 pages).
European Office Action issued in Appln. No. 10706804.1 dated Sep. 22, 2014 (4 pages).
Chinese Office Action issued in Appln. No. 201410098133.7 dated Jul. 3, 2015 with English Translation (16 pages).
Chinese Office Action issued in Appln. No. 201410098130.3 dated Jul. 31, 2015 with English Translation (8 pages).
United States Office Action issued in U.S. Appl. No. 13/138,194 dated Aug. 12, 2015 (24 pages).

* cited by examiner

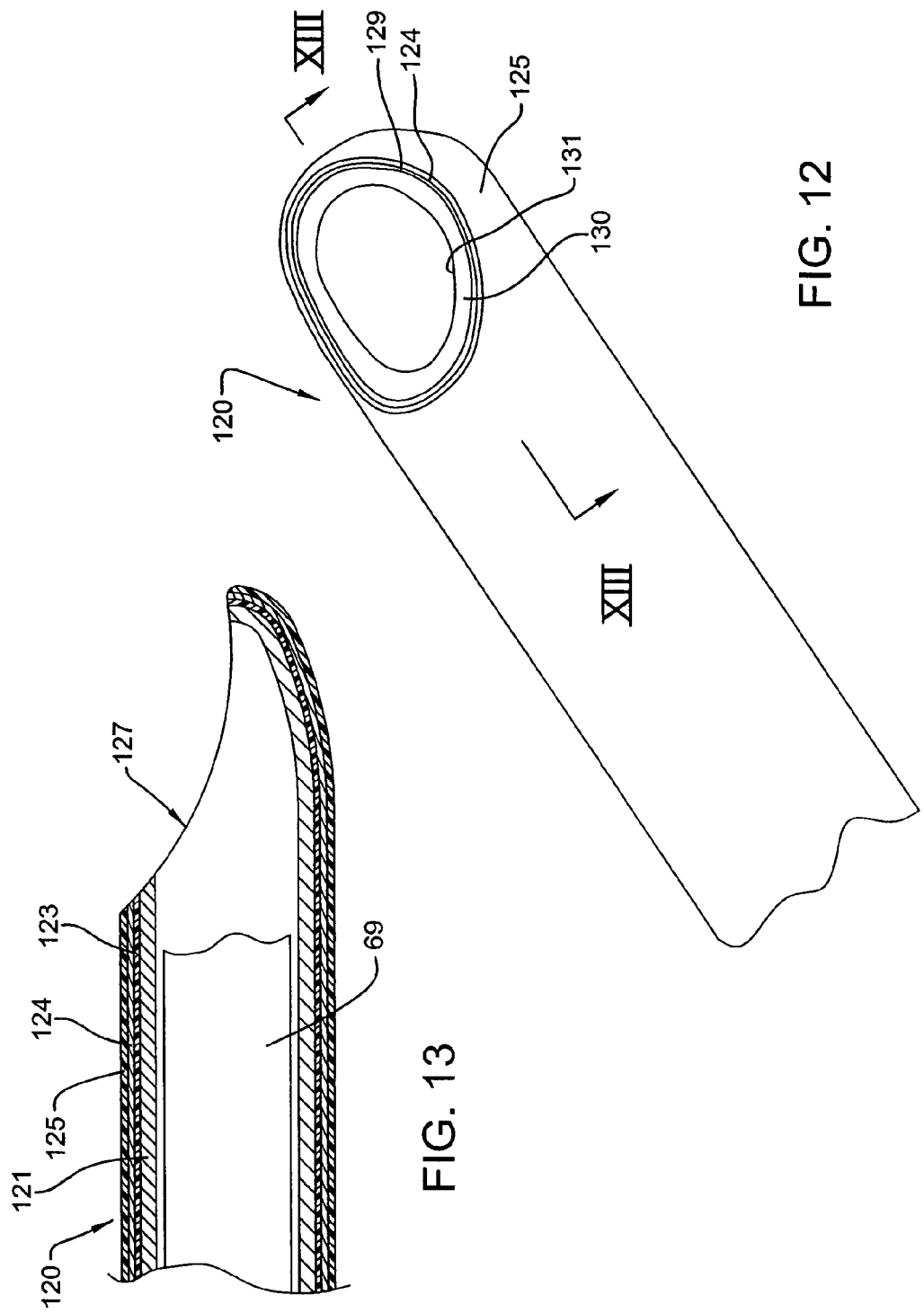

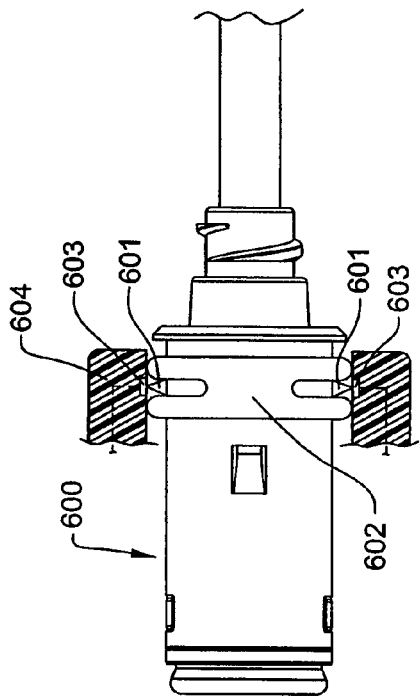
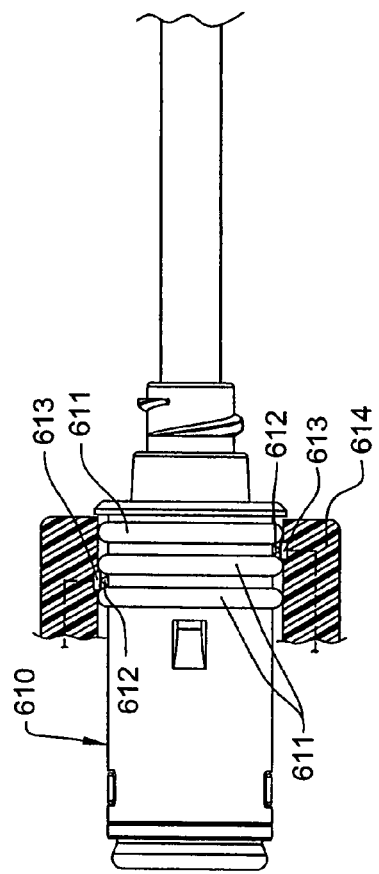
FIG. 28
FIG. 29

SURGICAL TOOL ARRANGEMENT

CROSS-REFERENCE TO RELATED APPLICATIONS

This is the National Stage of International Application No. PCT/US2006/009802, filed Mar. 17, 2006, which claims the benefit of U.S. Provisional Application No. 60/662,735, filed Mar. 17, 2005.

FIELD OF THE INVENTION

This invention is generally related to a surgical tool arrangement, and specifically to an arrangement which is capable of carrying out mechanical cutting, electrocauterization and ablation of tissue. The invention also relates to a universal surgical handpiece which is able to operate a number of different surgical tools or instruments which detachably connect to the handpiece.

BACKGROUND OF THE INVENTION

Surgical tools designed for mechanical cutting of tissue have been used for a number of years. These types of tools typically include a powered handpiece and a cutting tool which is secured in the distal end of the handpiece. The tool has an inner drive member including a hub drivingly engaged with an output shaft associated with a motor of the handpiece, and a drive shaft fixed to the hub which defines a cutting implement or head at a distal end thereof. An outer cannulated housing element is disposed about the drive shaft of the inner drive member and defines a cutting window thereon which cooperates with the moving cutting head to manipulate targeted patient tissue positioned adjacent the window.

Electrosurgical tools have also been available for many years, which tools employ electrical energy to treat targeted patient tissue in various ways. For example, electrocauterization is utilized to seal off and close blood vessels during surgery to prevent blood loss. In addition, ablation is utilized to vaporize or remove tissue using electrical energy. Electrosurgical probes are typically designed to perform both of these functions, depending upon the level of power supplied thereto. Further, monopolar and bipolar electrosurgical tools are conventional wherein monopolar tools direct electric current from an active electrode defined on the tool through the patient's body to a return electrode, which return electrode is typically defined by a grounding pad attached to the patient. Bipolar tools, on the other hand, include both an active and return electrode, wherein the current is directed from the active electrode to the return electrode through the contacted tissue.

Tools which are capable of both of the above functions are known. For example, U.S. Pat. No. 4,815,462 discloses a lipectomy device having a housing which mounts thereon an outer conduit, and a rotatable cutting blade disposed within the conduit. The rotatable cutting blade includes a distal end or tip which is interconnected to an electrical circuit which heats the tip so that same can be used for electrocoagulation of blood vessels.

U.S. Pat. No. 5,941,876 discloses a further electrosurgical rotating cutting device. This device incorporates an outer cannula structure in which a rotating cutting element is disposed. The outer cannula structure includes a commutator which effectively delivers electrical energy to the rotating cutter so that same serves as an active, energy delivering electrode. The device can be used as a monopolar instrument, for example by using the rotating cutter as an active electrode, and a remote grounding pad as the return electrode. Alternatively, the device can be used in a bipolar manner, by using an exposed portion of a sheath, which forms part of the outer cannula structure, as a return electrode.

One disadvantage of the above tools is that, since the rotating blade tip is utilized as the active, energy-delivering electrode, the surface area of the active electrode defined by the rotating blade tip varies, which can create inconsistent energy delivery and thus inconsistent performance.

U.S. Pat. No. 6,193,715 discloses an adapter unit for retrofitting on an existing surgical tool, such as a mechanical cutting implement, to convert same to a bipolar electrosurgical device. The device may also be used to convert a monopolar surgical device to a bipolar surgical device. The adapter unit includes a tubular sheath or conduit having a mounting block at one end of the sheath which is connected to a power source. The mounting block defines a pair of electrical signal connector pins. When the mechanical cutting device is positioned inside the adapter unit, one of these pins is in electrical connection with a conductive portion of the cutting device, and the other of the pins is electrically connected to a conductive intermediate layer of the sheath, which effectively converts the cutting device to a bipolar electrosurgical instrument. This adapter device, however, requires that an additional housing (i.e. the sheath) be placed over the existing housing of the cutting device, which significantly increases the overall size of the device, which in turn requires that a larger entry port be made in the patient.

In order to obviate or at least minimize the above disadvantages of known arrangements, the surgical tool arrangement according to the invention provides an integrated tool which detachably mounts to a powered handpiece and is of minimal overall size, does not utilize a rotating component for energy delivery to targeted tissue, and includes an active electrode provided on a stationary housing with a small surface area that enables improved energy delivery at the mechanical cutting interface. More specifically, the surgical tool arrangement includes an outer housing element including a hub arrangement which mounts to a coupling arrangement of the handpiece, and an elongated cannula or sheath fixed to the housing and in which a movable cutting element is disposed. The cannula defines an opening or window at a distal end thereof so as to expose the cutting head of the cutting element. Electrical energy is provided to an electrode arrangement provided on the cannula, and an electrode is defined immediately adjacent the window at the cutting interface. The electrical energy is returned via a grounding pad or alternatively via a conductive portion of the cannula.

Because the instant invention does not utilize the moving cutting element as an energy delivering electrode, the energy delivery at the cutting interface is consistent, thus resulting in more consistent tool performance. Further, since the moving cutting element is not utilized as an active electrode, there is no requirement to electrically isolate the mechanical cutting element from the outer housing element.

Further, the instant invention incorporates an electrical coupling between the handpiece and the integrated tool, which coupling provides electrical energy to the electrode arrangement of the integrated tool via the handpiece, thereby eliminating the need for a separate power cable.

Still further, the invention relates to a universal handpiece which is capable of accepting and operating a number of different surgical tools or instruments, each having one or multiple functions.

BRIEF DESCRIPTION OF THE DRAWINGS

FIG. 12 is an enlarged and fragmentary perspective view of the distal end of a fourth embodiment of the combined electrosurgical and cutting instrument;

FIG. 13 is an enlarged and fragmentary longitudinal cross-sectional view as seen generally along line 13-13 in FIG. 12;

FIG. 28 is a fragmentary view of an alternative hub and handpiece arrangement;

FIG. 29 is a fragmentary view of a further alternative hub and handpiece arrangement;

Figure 1:
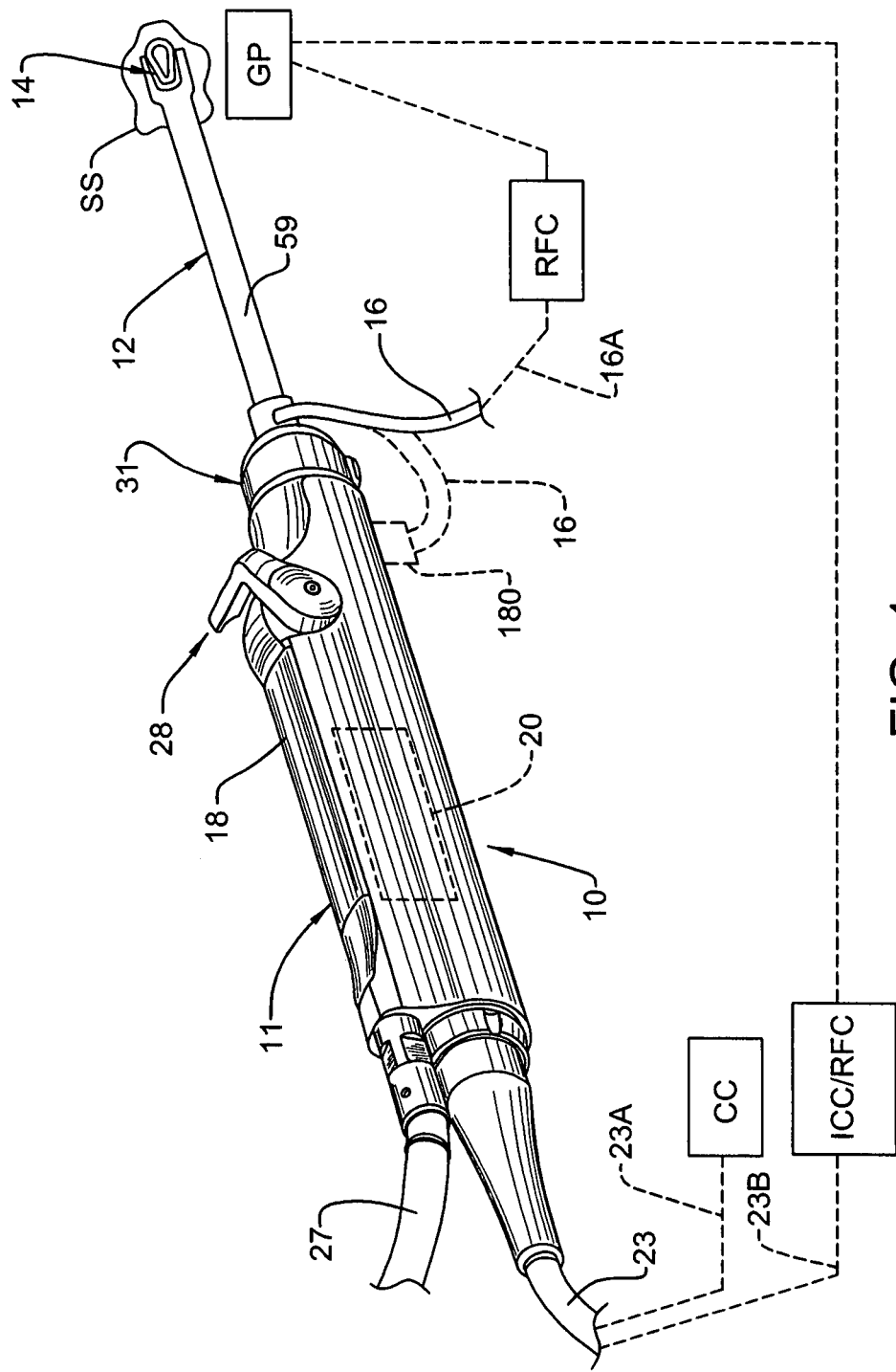
FIG. 1 is a perspective view of the surgical tool arrangement according to the invention.

Certain terminology will be used in the following description for convenience in reference only, and will not be limiting. For example, the words "upwardly", "downwardly", "rightwardly" and "leftwardly" will refer to directions in the drawings to which reference is made. The words "inwardly" and "outwardly" will refer to directions toward and away from, respectively, the geometric center of the arrangement and designated parts thereof. The words "forwardly" and "distally" will refer to the direction toward the end of the arrangement which is closest to the patient, and the words "rearwardly" and "proximally" will refer to the direction away from the end of the arrangement which is furthest from the patient. Said terminology will include the words specifically mentioned, derivatives thereof, and words of similar import.

DETAILED DESCRIPTION

Figure 3:
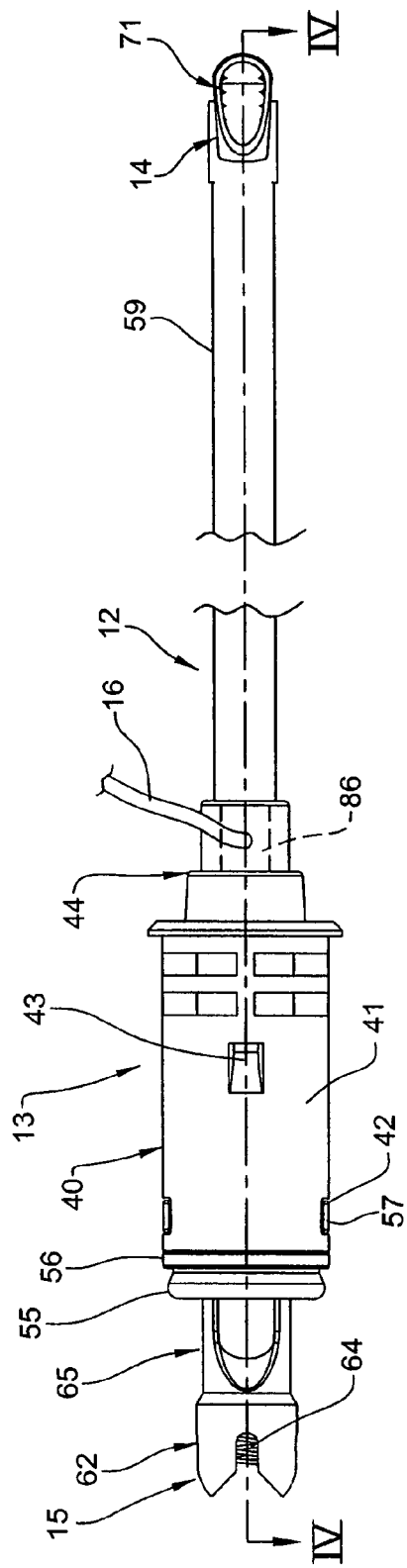
FIG. 3 is a fragmentary plan view of the combined electrosurgical and cutting instrument.

Referring to FIGS. 1 and 3, a surgical tool arrangement 10 according to the invention is illustrated. The arrangement 10 includes a handpiece 11, which at its distal end mounts thereon a combined electrosurgical and mechanical cutting instrument 12. The instrument 12 is comprised of an outer and generally tubular housing element 13 which includes an electrode 14 arrangement thereon, and a generally tubular and rotatable mechanical cutting element 15 mounted coaxially within housing element 13. In the illustrated embodiment, a cable 16 is mounted on housing element 13 for the purpose of supplying electrical energy to electrode arrangement 14.

Handpiece 11 is a commercially available surgical handpiece manufactured by the assignee hereof, under Model Nos. 375-704-500 and 375-701-500, and is accordingly only briefly described herein. Handpiece 11 includes an elongate outer housing 18 defining an elongate bore 19 therein. A motor 20 (shown diagrammatically only) is disposed within housing bore 19. Motor 20 includes an output or drive shaft 21, which drive shaft 21 mounts a drive pin 22 at the distal end thereof. A power cable 23 is coupled to the proximal end of handpiece 11 for supplying power to motor 20.

Handpiece housing 18 defines therein an elongate suction bore (not shown) extending generally parallel to and sidewardly of housing bore 19. This suction bore communicates with a diagonally extending suction passage 26 defined in housing 18, which passage 26 provides communication between the distal end of housing bore 19 and the suction bore. Suction is drawn through the handpiece 11 by a suction pump (not shown), which is connected to the handpiece 11 through a suction tube 27. Suction flow through the handpiece 11 is regulated by an adjustable valve 28. The above handpiece suction arrangement is described in detail in U.S.

Patent Application Publication No. 2003/0135151A1 published on Jul. 17, 2003, which is owned by the same assignee hereof and is hereby incorporated by reference herein.

The instrument 12 is removably attached to the distal end of handpiece 11 by a coupling assembly 31 provided on the handpiece 11. Coupling assembly 31 includes a generally ring-shaped collet 32 secured to the distal end of handpiece housing 18. A locking ring 33 is movably disposed in collet 32 and is biased to hold the instrument 12 within the housing bore 19 of handpiece 11. A release button 34 is provided on locking ring 33, and is used to release the locking ring 33 and allow removal of the instrument 12 from the handpiece 11. Further, a coil 35 is provided in a portion of the collet 32, which is used to facilitate inductive signal transfer to/from a radio frequency identification device (RFID) chip 36 disposed in the instrument 12.

Figure 2:
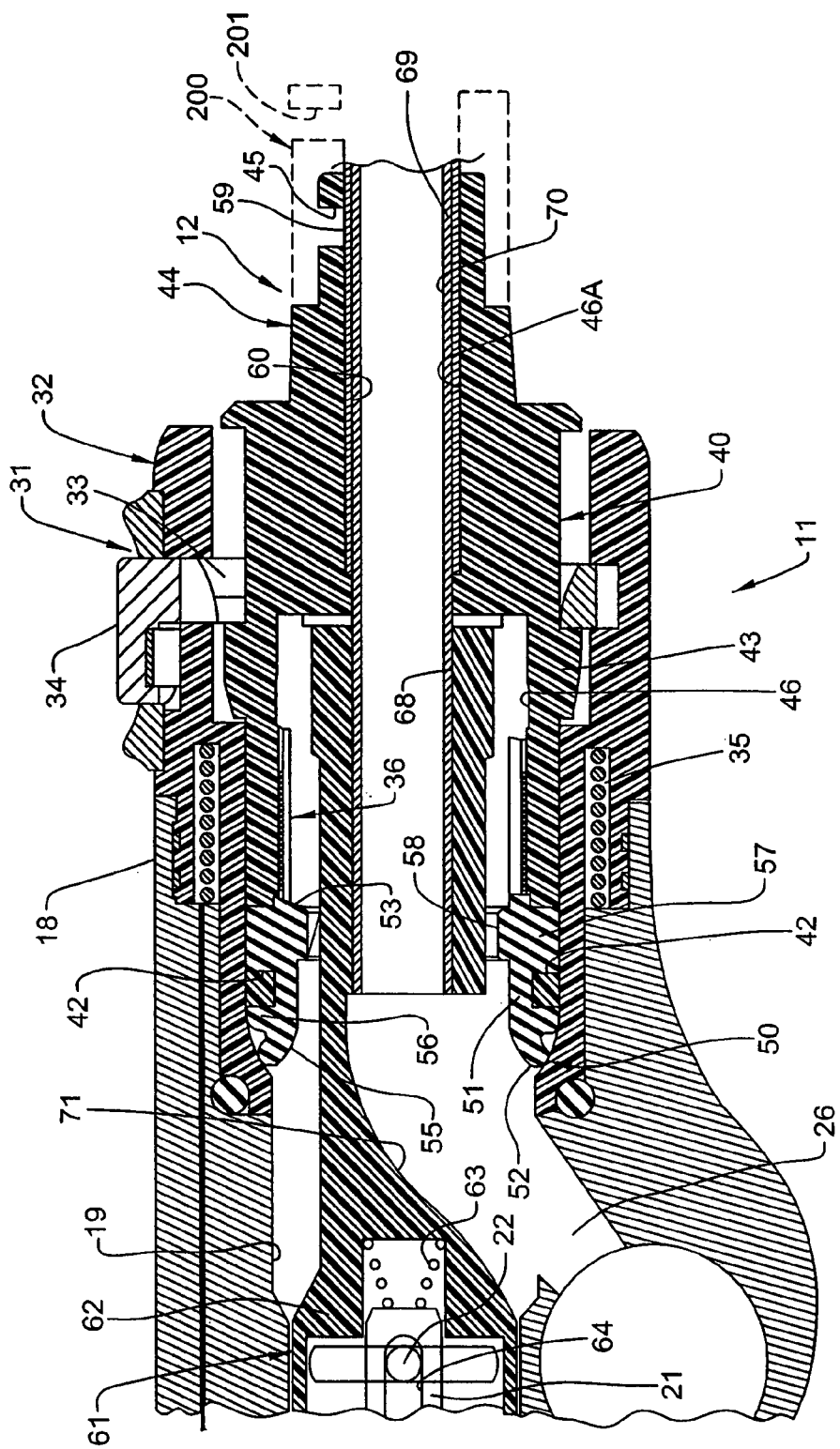
FIG. 2 is an enlarged, fragmentary longitudinal cross-sectional view of the surgical tool arrangement of FIG. 1.
Figure 4:
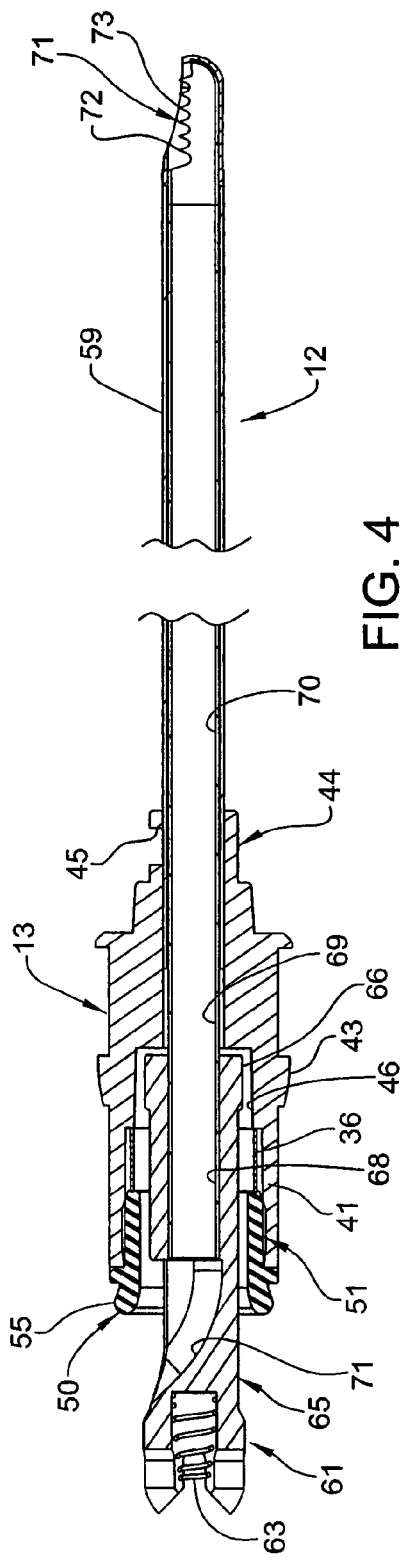
FIG. 4 is a fragmentary longitudinal cross-sectional view as seen generally along line 4-4 in FIG. 3.

Referring to FIGS. 2-4, the instrument 12 will now be described. Outer tubular housing element 13 includes a hub 40 which defines the proximal end of housing element 13. Hub 40 is defined by a generally tubular base body 41, which defines therein a pair of generally rectangular and diametrically-opposed openings 42 adjacent the proximal end thereof. Base body 41 also has formed thereon a pair of outwardly-projecting, diametrically opposed and generally ramp-shaped ears 43 disposed distally of openings 42. Ears 43 cooperate with coupling assembly 31 of handpiece 11 to secure instrument 12 therein. Hub 40 has a distal end defined by a head or nose 44 of a reduced diameter as compared to base body 41. In the illustrated embodiment, an opening 45 is defined in head 44 for receiving cable 16. Further, hub 40 defines therein a bore 46 which extends completely through the hub 40, and with which openings 42 of base body 41 and opening 45 of head 44 communicate.

An annular seal 50 is disposed within the proximal end of bore 46 of hub 40. Seal 50 is constructed of a resilient elastomeric material, and is defined by a main section 51 and axially-spaced proximal and distal sections 52 and 53 disposed at respective opposite ends of the main section 51. Proximal section 52 defines thereon a pair of annular ribs 55 and 56, which are disposed in sealing engagement with an inner annular surface of collet 32 of handpiece 11 when instrument is coupled thereto, as shown in FIG. 2. Distal section 53, as shown in FIGS. 2 and 4, defines thereon a pair of outwardly projecting and diametrically-opposed lock tabs 57 which engage within the respective openings 42 of hub 40 to secure the seal 50 to hub 40 and fix the axial position of seal 50 relative thereto. Distal section 53 additionally defines thereon a pair of inwardly projecting and diametrically-opposed stop tabs 58, which are generally radially aligned with the respective lock tabs 57. As best shown in FIG. 2, the chip 36, which, in the illustrated embodiment, is encapsulated within a ring structure, is seated within hub bore 46 of hub 40 axially adjacent the distal section 53 of seal 50.

The above-described coupling arrangement of handpiece 11 and the arrangement of coil 35 and chip 36 are disclosed in U.S. Patent Publication No. 2004-0220602A1 published on Nov. 4, 2004, owned by the same assignee hereof and hereby incorporated by reference herein.

Tubular housing element 13 additionally includes an elongate housing tube or cannula 59 which projects distally from hub 40. More specifically, housing tube 59 has a proximal end which is fixedly mounted within the distal portion of bore 46 of hub 40. Housing tube 59 itself defines an elongate bore or conduit 60 therein, in which the mechanical cutting element 15 is disposed, as discussed below.

Cutting element 15 is of a conventional construction, and will accordingly be only briefly described herein. Cutting element 15 includes a hub 61 which defines the proximal end thereof. The hub 61 includes a motor-engaging drive hub 62 defining a proximally opening bore therein in which a coil spring 63 is located, and a slot 64 which extends transversely to the longitudinal axis of the cutting element 15. Hub 61 additionally includes a neck 65 which extends distally from drive hub 62. Neck 65 terminates at a head 66 which has an enlarged outer diameter as compared to the remainder of neck 65. In this regard, the outer diameter of head 66 is slightly larger than the inward projection of the respective stop tabs 58 of seal 50. A bore 68 extends through neck 65 and head 66, in which an elongate and tubular drive shaft 69 is fixed. Drive shaft 69 defines therein a suction passage 70 which is in communication with a suction port 71 defined in neck 65, which suction port 71 is in turn in communication with suction passage 26 of handpiece 11.

Figure 5:
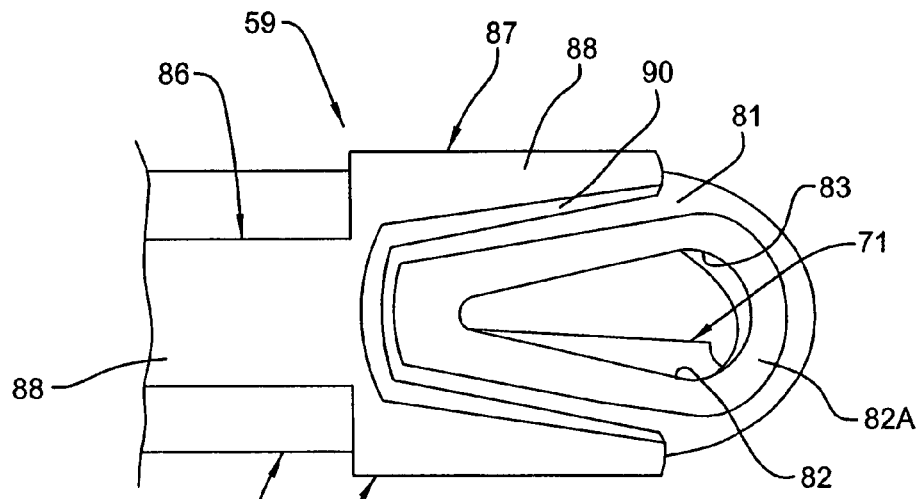
FIG. 5 is an enlarged and fragmentary plan view of the distal end of the combined electrosurgical and cutting instrument.

Drive shaft 69 includes a cutting element or head 71 at its distal end thereof. Cutting head 71 defines therein a window or opening 72 which communicates with suction passage 70. In the illustrated embodiment, the cutting head 71 includes a plurality of teeth 73 disposed along and defining window 72 for severing tissue. However, it will be appreciated that drive shaft 69 may include other types of cutting heads, such as those with non-toothed or straight cutting edges as shown in FIG. 5, a burr, etc.

Figure 6:
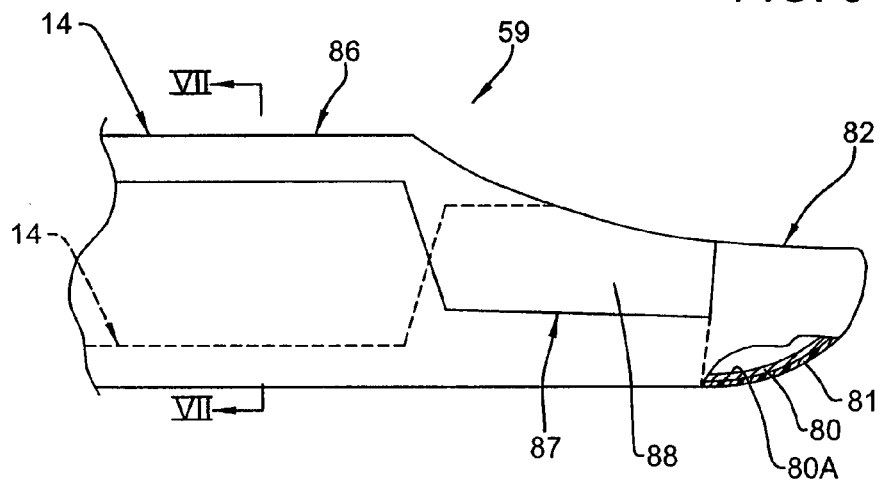
FIG. 6 is an enlarged and fragmentary side view of the combined electrosurgical and cutting instrument of FIG. 5.
Figure 7:
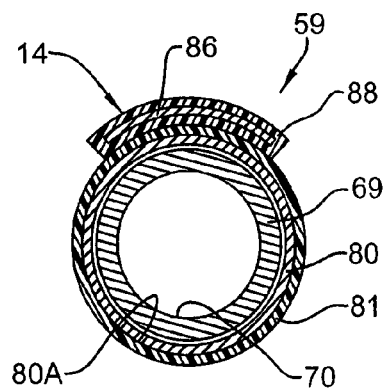
FIG. 7 is an enlarged transverse cross-sectional view as seen generally along line 7-7 in FIG. 6.

The structure of housing tube 59 of housing element 13 will now be described with reference to FIGS. 5-7. Housing tube 59 is defined by an elongate and rigid tube 80, which in the illustrated embodiment is constructed of metal, such as stainless steel. Tube 80 defines a bore 80A therein, in which the drive shaft 69 of cutting element 15 is movably disposed. The outer surface of tube 80 is covered with an insulating material 81, such as, for example, by powder-coating tube 80. The distal end of housing tube 59, including tube 80 and insulating layer 81, is cut so as to define a window 82 which in the illustrated embodiment opens generally sidewardly of the tube 80, such that the housing tube 59 has a distal end which is generally closed in the axial direction. The cutting of the tube 59 results in a ring-like portion 82A of the tube 80 being exposed inwardly of the outer insulating layer 81, which exposed ring-like portion 82A defines a ring-shaped cutting edge 83 which cooperates with cutting head 71 of cutting element 15 to sever tissue. Alternatively, the housing tube 59 may be cut vertically so as to define a cutting window which is centered on the axis of the tube 59, such that the tube 59 is open in the axial direction at its distal end.

Housing tube 59 includes the electrode arrangement 14 which is secured to tube 80 over the insulating layer 81 thereof. Electrode arrangement 14 in the illustrated embodiment is defined by an electrically-conductive strip-like electrode element having an elongated and proximally-oriented portion 86 and a distal portion 87 oriented transversely relative to portion 86. Proximal portion 86 extends rearwardly from portion 87 along outer layer 81 of tube 80 and into a distal portion 46A (FIG. 2) of hub bore 46 and distal portion 86 is disposed adjacent window 82 of tube 59. Prior to assembly of electrode arrangement 14 to tube 80, electrode 14 is generally T-shaped. As shown in FIGS. 6 and 7, portions 86 and 87 of electrode 14 are coated on all exterior sides thereof with an insulating material 88, such as, for example, by powder-coating. Portions 86 and 87 of electrode arrangement 14 in the illustrated embodiment are constructed of conductive metal, such as stainless steel or tungsten. However, other suitable materials may be utilized.

In the illustrated embodiment, electrode arrangement 14 is formed from an elongate tubular member of a similar outer diameter as tube 80 and insulating layer 81. Distal portion 87 is thus arcuately curved and is press-fitted to the distal end of tube 59. The whole assembly is then baked to cure the insulating layers 81 and 88. During baking, the insulating layer 88 located on the bottom of the portions 86 and 87 and the insulating layer 81 of tube 80 join to one another, which effectively secures proximal portion 86 along the length of tube 80. Alternatively, or in addition to the above, the electrode arrangement 14 can be adhesively secured to tube 59.

In the illustrated embodiment, the electrode arrangement 14, being formed from a tubular member, is essentially wrapped partially around the outer circumference of layer 81 of tube 80. In this regard and in one embodiment, the distal portion 87 circumferentially overlaps the tube 80 by approximately 200 degrees. This allows the distal portion 87 of electrode arrangement 14 to be cut at the same time the window 82 is formed in the tube 59 as discussed above.

Thus, once electrode arrangement 14 is secured to the outer layer 81 of tube 80, the entire assembly at its distal end is then cut. This cutting process results in exposure of a part of the conductive material of distal portion 87 inwardly of the insulating layer 88, as shown in FIG. 5. This exposed portion defines a generally U-shaped electrode 90 disposed in partially surrounding relation with cutting edge 83 of tube 80. The electrode 90 is surrounded on its proximally-facing side by insulating layer 88 of portion 87, and on its distally-facing side by insulating layer 81 of tube 80. Due to the limited surface area of electrode 90, a high-density-current can be delivered to the surgical site.

As mentioned briefly above, the proximal portion 86 of electrode arrangement 14 extends rearwardly along outer layer 81 of tube 80 and into portion 46A of hub bore 46. In this regard, the uppermost insulating layer 88 is removed from the terminal proximal end of portion 86, or alternatively the terminal proximal end of portion 86 is not initially coated with insulating layer 88 (for example by masking), to allow electrical connection thereof to cable 16, as shown in dotted lines in FIG. 3. Cable 16 thus supplies electrical power to electrode arrangement 14 through the proximal terminal end of portion 86.

As shown in dotted lines in FIG. 2, an alternative method of connecting cable 16 to electrode arrangement 14 is to provide a sleeve-like cap 200 secured over head 44 of hub 40 via a threaded engagement, adhesive or other suitable fastening arrangement. In this embodiment, instead of providing opening 45 in head 44, a similar opening 201 is defined in cap 200 for receiving cable 16. Portion 86 of electrode arrangement would thus be electrically connected to cable 16 distally from head 44.

It will be appreciated that the electrode arrangement 14 can be positioned on tube 80 at various circumferential locations which would then result in a variety of different electrode configurations at the distal end of tube 59. For example, the electrode arrangement 14 can be positioned on the lower side of tube 80, instead of along the upper side thereof. The electrode arrangement 14 can then be cut along with tube 80 to form the window at the distal end of the housing tube 59. This alternative embodiment is illustrated in dotted lines in FIG. 6. Positioning the electrode arrangement 14 in this manner would result in an electrode defined by a pair of laterally-spaced, strip-like areas located on opposite sides of the cutting edge 83 of tube 80.

The cutting element 15 is assembled to the outer housing element 13 by inserting the distal end of drive shaft 69 of cutting element 15 into bore 46 at the proximal end of hub 40. During this insertion, the enlarged head 66 of hub 61 compresses the seal 50 and head 66 pushes past the stop tabs 58, at which point the seal 50 resumes its original shape. The stop tabs 58, while allowing some axial displacement of cutting element 15 relative to housing element 13, prevent the cutting element 15 from detaching or falling out of the outer housing element 13 due to gravitational forces.

The assembled instrument 12 is secured to the handpiece 11 in a similar manner to that described in the '602 publication referenced above, and will accordingly be only briefly described herein. Instrument 12 is attached to the handpiece 11 by inserting the hubs 40 and 61 into the open distal end of collet 32. The ears 43 of hub 40 seat within the collet 32, and the locking ring 33 serves to hold the instrument 12 within handpiece 11. The above securement of the tool 12 to handpiece 11 causes the drive hub 62 to engage the motor output shaft 21. More specifically, the pin 22 of shaft 21 seats within slot 64 of drive hub 62, such that the rotational movement of the shaft 21 is transferred to the cutting element 15. The spring 63 of drive hub 62 biases the cutting element 15 forwardly or in the distal direction, so as to maintain the cutting head 71 of cutting element 15 in bearing contact with the interior of the closed distal end of the static housing tube 59 of outer housing element 13.

While cutting element 15 is described herein as including a drive shaft 69 and cutting head 71 which are rotatable relative to tube 59 of outer housing element 13, it will be appreciated that cutting element 15 may alternatively include a component which moves axially or translationally relative to tube 59.

In operation, the distal end of tool 10 is inserted into the surgical site SS (FIG. 1), and can be utilized to perform multiple functions simultaneously or separately from one another. If desirable or necessary, the distal end of tool 10 can be inserted into the surgical site through a working portal defined by a conventional cannula or trocar (not shown). The mechanical cutting element 15 of tool 12 is controlled by a cutter control (CC) connected to handpiece cable 23 as shown by dotted line 23A in FIG. 1, which control (CC) supplies electrical power to the motor 20 of handpiece 11 in order to actuate cutting element 15. Control (CC) also controls the mode of operation of cutting element 15, for example by controlling motor so as to drive cutting element 15 in a forward or reverse direction, or in an oscillating manner, as is conventional. If mechanical cutting of tissue is desired, then motor 20 is activated so as to cause cutting element 15 to rotate within and relative to outer housing element 13. The cutting head 71 of cutting element 15 and the teeth 73 thereof are rotated past cutting edge 83 of static housing tube 80, which effectively cuts tissue located adjacent or within cutting window 72.

The tool 10 is also operable as an electrosurgical tool for the purpose of cauterizing or ablating tissue. These functions are controlled by a radio frequency control (RFC) connected to cable 16 as shown by dotted line 16A in FIG. 1 which includes an electrosurgical generator. The generator is capable of generating two types of radio frequency electrosurgical waveforms or signals, namely, a low power signal which enables electrode 90 to coagulate fluid, such as blood, to seal tissue at the surgical site (SS), and a high power signal which enables electrode element 90 to vaporize tissue or remove same. If the surgeon selects the coagulation mode, then the RF control (RFC) sends the appropriate signal to electrode arrangement 14 via cable 16, so as to apply electrical current to the targeted tissue through electrode 90. In one embodiment, the tool 10 is operated as a monopolar tool, and thus a grounding pad (GP) is firmly affixed to the patient in an area that is electrically near the surgical site (SS) in a known manner. The grounding pad (GP) defines the return path for the electrical current to the RF control (RFC). The surgeon can also select the ablation mode if tissue removal (or "cutting") is desired. Alternatively, the tool 10 may be configured to operate in only one mode in addition to mechanical cutting, i.e. either an electrocautery mode or an ablation mode.

Tool 10 can also be operated to perform both cauterization with electrode 90 and mechanical cutting with cutting element 15 at the surgical site (SS). The application of current to the targeted tissue simultaneously with mechanical cutting via cutting head 71 causes heating of the targeted tissue, which may result in easier and more efficient cutting of tissue. In this regard, the current applied to the targeted tissue through electrode 90 may tend to firm up or harden the tissue, which may result in a more precise cut by cutting element 15. Further, tool 10 can be operated to perform both ablation with electrode 90 and mechanical cutting with element 15, if desirable or necessary.

It will be appreciated that when desirable or necessary, cut tissue and other surgical debris or fluids can be removed by suction through window 72 and suction passage 70 of drive shaft 69, through suction port 71 and suction passage 26, and ultimately through suction tube 23.

The tool 10 according to the invention can thus be operated in a mechanical cutting mode by activating cutting element 15, in cauterization or ablation modes by activating electrode 14, or in a simultaneous mechanical cutting mode and cauterization or ablation mode by activating both cutting element 15 and electrode 14.

It will be appreciated that the cutter control (CC) may include appropriate control buttons so as to allow the surgeon or operator to select the desired cutter operations. These control functions of the cutter may alternatively be performed directly from the handpiece 11 which would then include the appropriate control buttons. Likewise, the RF control (RFC) may include appropriate control buttons so as to allow the surgeon to select the desired power levels and operating modes.

Alternatively, each of these controls (CC) and (RFC) may be associated with a switch, either through a suitable cable or wirelessly, to allow the surgeon to operate the controls remotely. Such a switch may be a footswitch or a hand switch. A single foot or hand switch may also be utilized to control both functions or modalities of the tool 10 by providing two buttons or controls on the switch. The functions of cutter element 15 would be mapped to one button, and the functions of electrode arrangement 14 would be mapped to the other button. This would allow the surgeon to operate the tool 10 in the mechanical cutting mode or the electrosurgical mode independently of one another, and also allow the surgeon to operate the tool 10 so that mechanical cutting of tissue and electrosurgical treatment of the tissue occur simultaneously with one another. Alternatively, a single button provided on the switch can be mapped with the functions of both cutting element 15 and electrode arrangement 14, so that the single button when actuated will always activate cutting element 15 and electrode arrangement 14 simultaneously.

FIG. 1 illustrates an alternative arrangement of cable 16. More specifically, handpiece 11 incorporates a cable connector 180 (shown in dotted lines) which projects from housing 18 and is configured to accept a connector associated with the terminal end of cable 16 (also shown in dotted lines). In this embodiment, electrode arrangement 14 and cutting element 15 can be controlled by an integrated cutter control and RF control (ICC/RFC) which is connected to cable 23 of handpiece 11 as shown by dotted line 23B in FIG. 1. Suitable electrical wiring would then be provided through the handpiece 11 for powering the electrode arrangement 14. Alternatively, a cutter control (CC) and an RF control (RFC) may be provided as separate control units which are then connected in a daisy-chain fashion to one another.

Figure 8:
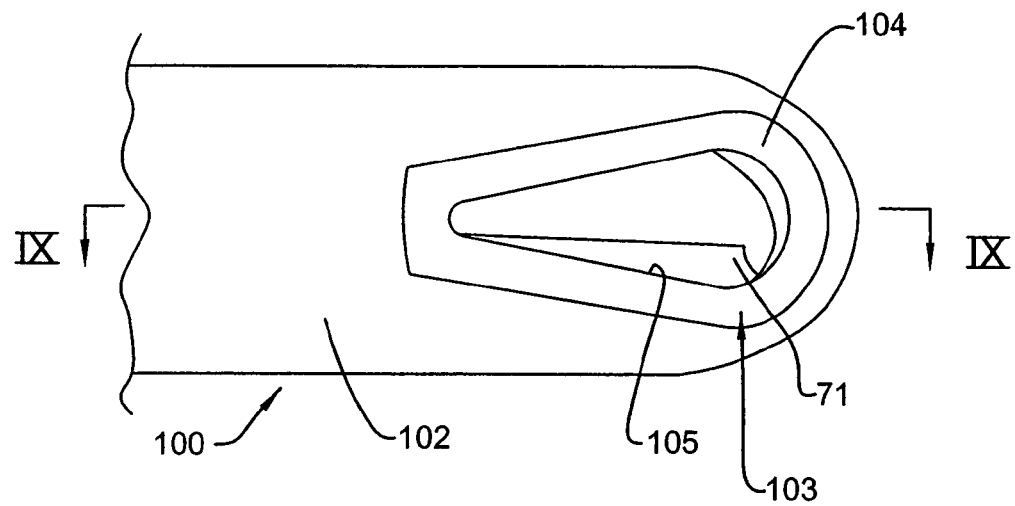
FIG. 8 is an enlarged and fragmentary plan view of the distal end of a second embodiment of the combined electrosurgical and cutting instrument.
Figure 9:
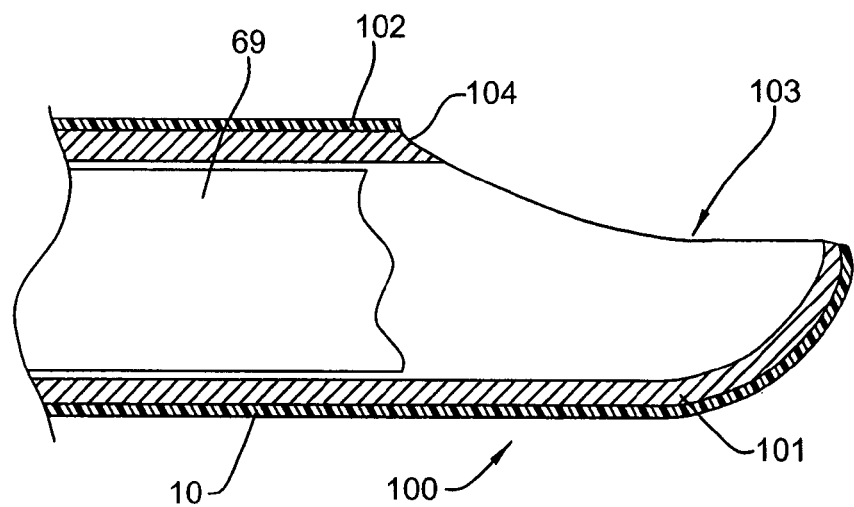
FIG. 9 is an enlarged and fragmentary longitudinal cross-sectional view as seen generally along line 9-9 in FIG. 8.

FIGS. 8 and 9 illustrate a second embodiment of a combined electrosurgical tool and cutting instrument 100 which may be utilized with handpiece 11. The instrument 100 includes a static housing tube 101 which houses therein the rotating drive shaft 69 of cutting element 15. Housing tube 101 in the illustrated embodiment is constructed of a conductive metal, for example stainless steel, and is coated on its outer surface thereof with an insulating material 102. Housing tube 101 with its insulating layer 102 is then cut as described above with respect to the first embodiment to define a window 103 at the distal end of instrument 100. This cutting process exposes a ring-like or annular area 104 of housing tube 101 located inwardly of insulating layer 102. Area 104 defines both an active electrode for delivering electrical current to the surgical site SS at window 103, and also defines a cutting edge 105 which cooperates with the cutting head 71 of cutting element 15 to sever tissue. In order to deliver electrical current to area 104, the insulating layer 102 is removed from the proximal end of housing tube 101 located within head 44 of hub 40 (or alternatively a portion of the proximal end of housing tube 101 is not initially provided with layer 102), and housing tube 101 is electrically connected to cable 16. The electrical current delivered to surgical site (SS) through area 104 is returned via the patient grounding pad (GP) as discussed above.

Figure 10:
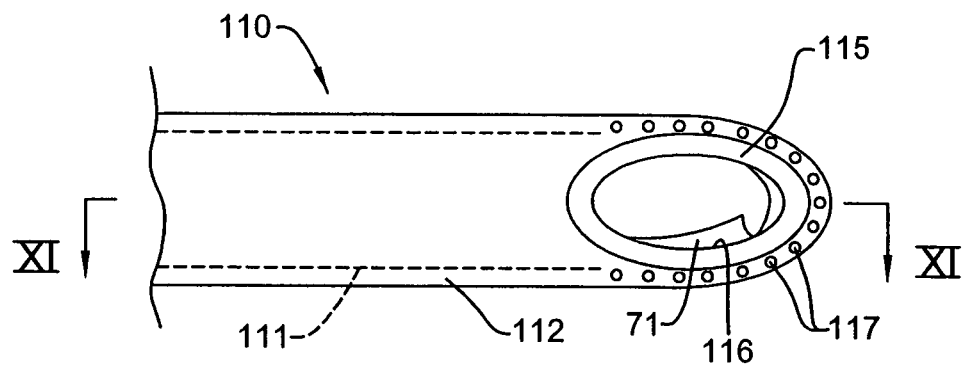
FIG. 10 is an enlarged and fragmentary plan view of the distal end of a third embodiment of the combined electrosurgical and cutting instrument.
Figure 11:
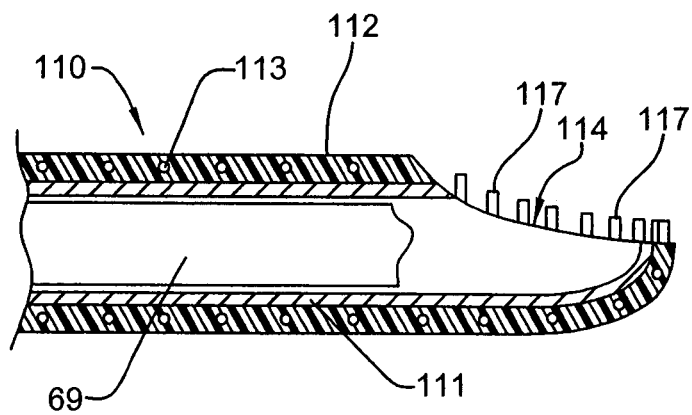
FIG. 11 is an enlarged and fragmentary longitudinal cross-sectional view as seen generally along line 11-11 in FIG. 10.

FIGS. 10 and 11 illustrate a third embodiment of a combined electrosurgical tool and cutting instrument 110 which may be utilized with handpiece 11. In this embodiment, the instrument 110 includes an inner housing tube 111 constructed of metal, for example stainless steel. An outer housing tube 112 is disposed over the inner tube 111 and is non-movable relative thereto. Outer tube 112 is constructed of rigid plastic, and includes a conductive wire mesh or coil 113 embedded therein. The respective tubes 111 and 112 are then cut as described above to define a window 114 at the distal end of instrument 110, as in the above embodiments. The cutting process exposes a ring-shaped area 115 of inner tube 111, inwardly of the edge of outer tube 112. Area 115 defines a cutting edge 116 which cooperates with the cutting head 71 of cutting element 15 to sever tissue. After cutting of the instrument 110 to define window 114, the plastic of outer tube 112 is removed around portions of the wire mesh 113 to define a plurality of electrodes 117 which are oriented around and outwardly of cutting edge 116 of inner tube 111. In order to deliver electrical current to the electrodes 117, the wire mesh 113 at the proximal end of outer tube 112 is exposed or stripped of the plastic material of tube 112 and is electrically connected to cable 16. The electrodes 117 serve to deliver electrical current to the surgical site (SS), which current is then returned via the patient grounding pad (GP). In this embodiment, due to the small size of the respective electrodes 117, high-density current can be delivered to the surgical site (SS).

The first three embodiments of the combined electrosurgical tool and cutting instrument are disclosed herein as being utilized as monopolar instruments in conjunction with a patient grounding pad (GP). However it may be possible or desirable to utilize some of these instruments as bipolar instruments. For example, and with respect to the first embodiment of FIGS. 5-7, the housing tube 80 and its exposed ring-like portion 82A can be used as the return path for the electrical current delivered to the surgical site (SS) via electrode arrangement 14. In this instance, the insulating layer 81 can be removed from (or not initially applied to) an area located on the proximal end of housing tube 80 inside head 44 of hub 40, and then electrically connected to cable 16, wherein cable 16 would be configured to both deliver electrical current to electrode arrangement 14 from RF control (RFC) and return current from housing tube 80 to RF control (RFC).

With respect to the third embodiment illustrated in FIGS. 10 and 11, the housing tube 111 and its exposed ring-like area 115 can be used as the return path for the electrical current delivered to the surgical site (SS) via electrodes 117. In this regard, it may be desirable or necessary to leave only small portions of the tips of electrodes 117 exposed so that a greater distance is defined between the electrode tips and the return area 115 to prevent arcing of the current.

FIGS. 12 and 13 illustrate a fourth embodiment of a combined electrosurgical and cutting instrument 120 which may be utilized with handpiece 11. In this embodiment, instrument 120 is a multi-layer component. More specifically, instrument 120 includes an innermost housing tube 121 of a conductive material, such as stainless steel. The outer surface of tube 121 is coated with an insulating layer 123. The insulating layer 123 is covered with a conductive layer 124, such as copper, and the conductive layer 124 is covered with a further insulating layer 125. In this embodiment as in the prior embodiments, the instrument 120 is cut at its distal end to define a window 127, which cutting process results in the formation of an annular electrode 129 defined by the exposed distal end of the conductive layer 124. The exposed distal end of inner housing tube 121 defines a ring-like area 130, the innermost edge of which defines a cutting edge 131 which cooperates with cutting head 71 of cutting element 15 to sever tissue during rotation of cutting head 71 within tube 121.

The above embodiment is intended for operation as a bipolar instrument. In this regard, the outermost insulating layer 125 is removed from (or not initially applied to) a portion of the proximal end of the instrument 120 to expose conductive layer 124 and allow electrical connection of same to cable 16. Electrical current is thus delivered from RF control (RFC) through cable 16 to conductive layer 124 and to the surgical site (SS) via electrode 129. The electrical current is returned to the RF control (RFC) via housing tube 121 and its ring-like area 130.

Alternatively, the instrument 120 can be utilized as a monopolar instrument. In this instance, electrical current is delivered to the surgical site (SS) via electrode 129, but is returned via the grounding pad (GP). The inner housing tube 121 in this instance thus serves solely to define a cutting edge 131 for cooperating with cutting head 71.

Figure 14:
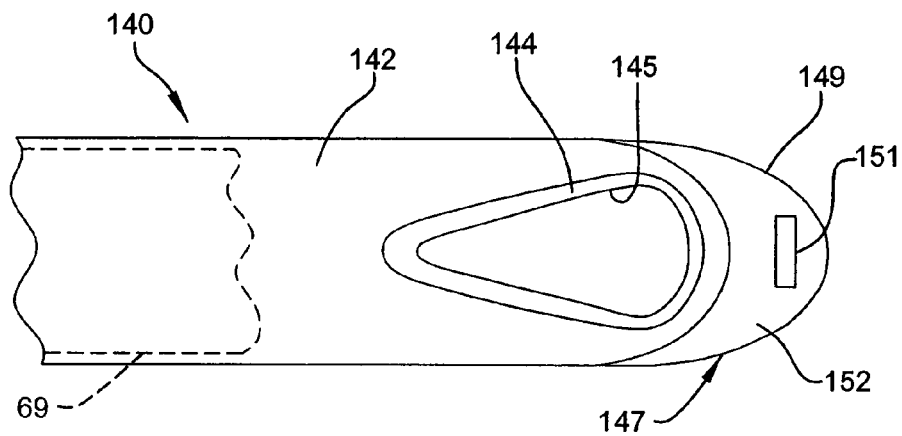
FIG. 14 is an enlarged and fragmentary plan view of the distal end of a fifth embodiment of the combined electrosurgical and cutting instrument.
Figure 15:
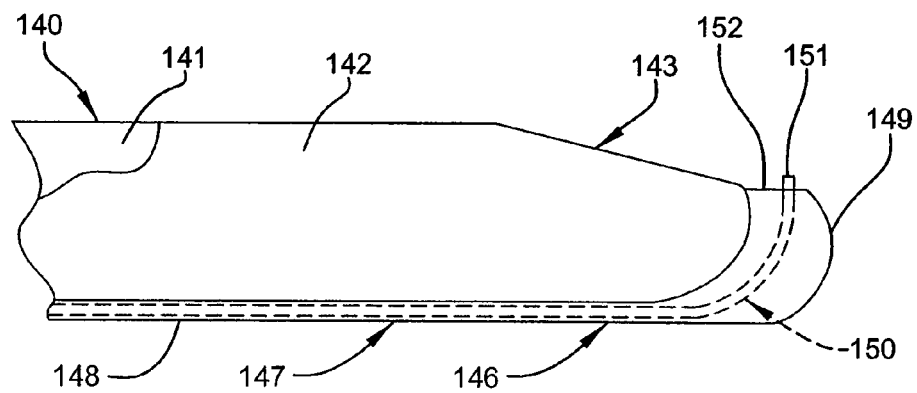
FIG. 15 is an enlarged and fragmentary side view of the combined electrosurgical and cutting instrument of FIG. 14.

FIGS. 14 and 15 illustrate a fifth embodiment of a combined electrosurgical tool and cutting instrument 140 which may be utilized with handpiece 11. The instrument 140 includes a static housing tube 141 which houses therein the drive shaft 69 of cutting element 15. Housing tube 141 in the illustrated embodiment is constructed of a conductive metal, such as stainless steel, and is coated on its outer surface with an insulator 142. Housing tube 141 along with its insulator 142 is then cut as described above to define a window 143 at the distal end of instrument 140. This cutting process exposes a ring-like area 144 of housing tube 141 located inwardly of insulating layer 142. Area 144 defines a cutting edge 145 which cooperates with cutting head 71 of cutting element 15 to sever tissue.

Instrument 140 additionally includes an electrode arrangement 146 fixedly mounted on housing tube 141 over insulator 142. Electrode arrangement 146 includes an elongate insulating element 147 which in the illustrated embodiment is of a ceramic or other suitable material. Insulating element 147 has a strip-shaped proximal portion 148 which extends along and overlies the outer lower surface of insulator 142, and a distal portion or head 149 which projects generally upwardly from proximal portion 148 and overlies the closed distal end of housing tube 141. Embedded within insulating element 147 is an electrode member 150 defining an active electrode or tip 151 which projects upwardly beyond an upper surface 152 of insulating element 147. The remainder of electrode element 150 extends downwardly from tip 151 and then proximally along the lower surface of housing tube 141, as illustrated in dotted lines in FIG. 15.

In order to deliver electrical current to electrode 151, a proximal portion of electrode element 150 exposed from insulating material of element 147 is electrically connected to cable 16. In one embodiment, the instrument 140 is utilized as a monopolar device, and thus the electrical current delivered to the surgical site (SS) through electrode 151 is returned via the patient grounding pad (GP) as discussed above.

In another embodiment, it may be possible to utilize the instrument 140 as a bipolar device. In this instance, the exposed area 144 of housing tube 141 defines a return electrode. As such, the housing tube 141 at its proximal end is exposed through insulator 142 so as to allow electrical connection of housing tube 141 to cable 16. Cable 16 would accordingly be configured to both deliver electrical current to electrode arrangement 146 from RF control (RFC) and to return current from housing tube 141 to RF control (RFC).

Figure 16:
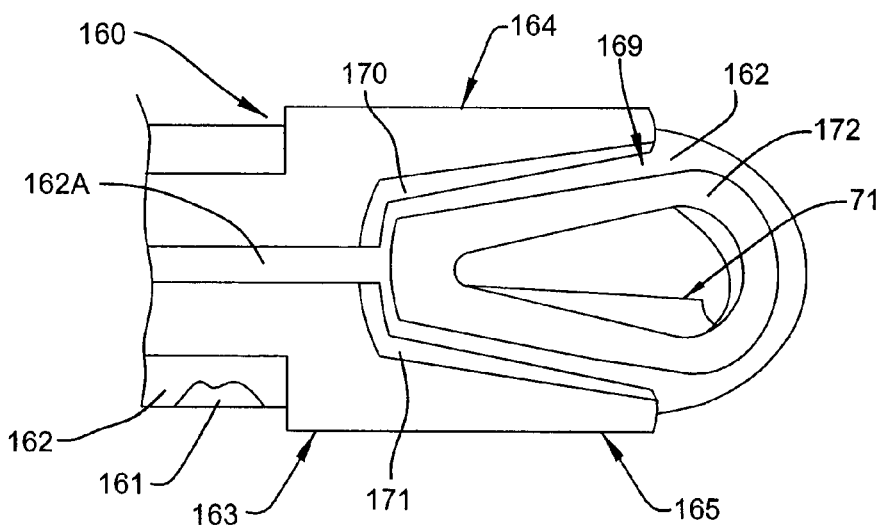
FIG. 16 is an enlarged and fragmentary plan view of the distal end of a sixth embodiment of the combined electrosurgical and cutting instrument.

FIG. 16 illustrates a sixth embodiment of a combined electrosurgical tool and cutting instrument 160 which is usable with handpiece 11. Instrument 160 includes a static housing tube 161 constructed of a metal material such as stainless steel, in which the drive shaft 59 (not shown here) of cutting element 15 is movably disposed. The outer surface of tube 161 is covered with an insulator 162. An electrode arrangement 163 is secured to tube 161 over insulator 162 thereof. Electrode arrangement 163 is identical to electrode arrangement 14, except that same is bifurcated or split longitudinally along the length thereof to define a pair of electrode elements 164 and 165 which are mirror images of one another and oriented in side-by-side relation over insulator 162 of housing tube 161. Further, electrode elements 164 and 165 are laterally spaced and thus separated from one another by an exposed longitudinal strip 162A of the housing insulator 162.

The electrode arrangement 163 is secured over insulator 162 of housing tube 161 as in the first embodiment, and the distal end of the electrode arrangement 163 is cut at the same time with housing tube 161 and insulator 162 to define a window 169. The cutting process results in the exposure of distal portions of the respective electrode elements 164 and 165 inwardly of insulator 162. These exposed portions respectively define generally L and J-shaped electrodes 170 and 171, which are disposed in partially surrounding relation with an exposed annular area 172 (also formed as a result of the cutting process) of housing tube 161 and separated therefrom by insulator 162.

The embodiment of FIG. 16 is intended for operation as a bipolar instrument, wherein one of the electrodes 170 or 171 defines an active, energy-delivering electrode, and the other electrode defines a return electrode. Exposed area 172 of tube 161 defines a cutting edge which cooperates with cutting head 71 of cutting element 15. Cable 16 is electrically connected to both the active and return electrodes 170 and 171 at proximal exposed ends thereof.

The various embodiments of the electrode arrangements are disclosed herein as having distal ends which are cut simultaneously with the distal end of housing tube. However, it will be appreciated that the distal end of the electrode arrangement, and thus the configuration of the electrode thereof, may be formed separately from the cutting window of the housing tube, and the electrode arrangement subsequently positioned on and fixed to housing tube.

Figure 17:
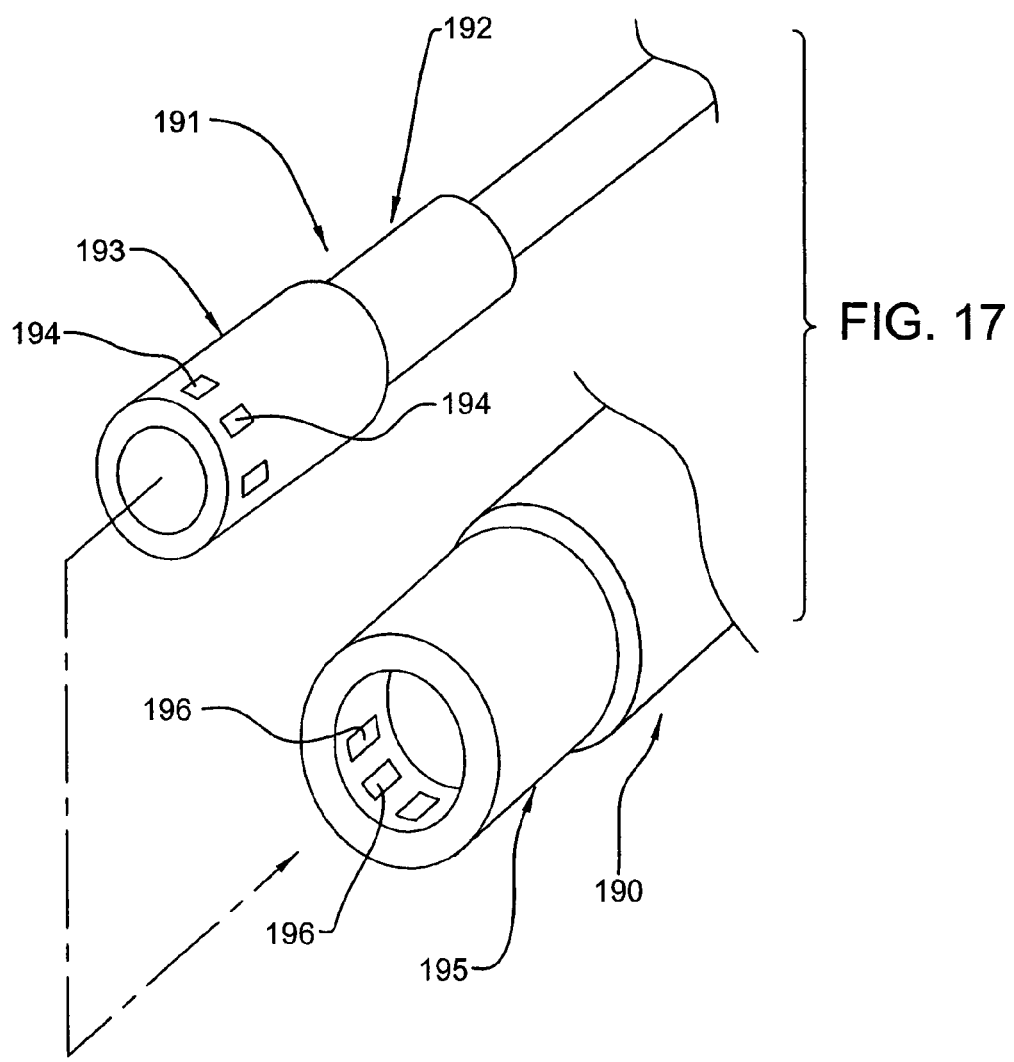
FIG. 17 is an enlarged and fragmentary exploded view of an alternative embodiment of a surgical tool arrangement according to the inventions.

FIG. 17 illustrates an alternative configuration of the handpiece and hub of the combined electrosurgical and cutting instrument, wherein only the distal end of handpiece 190 and the proximal end of the combined electrosurgical and cutting instrument 191 are illustrated for simplicity. The distal end of instrument 191 may be configured according to any of the above embodiments. Instrument 191 includes an outer tubular housing element 192 with a hub 193, in which the cutting element 15 (not shown here) is disposed. Hub 193 incorporates one or more conductive spring contacts or blades 194, which in the illustrated embodiment are distributed circumferentially along a portion of the outer surface of hub 193 at the proximal end thereof. Contacts 194 are electrically connected to the electrode arrangement (not shown here, but see FIG. 25) of housing element 192. Handpiece 190 includes a collet 195, similar to collet 32 discussed above, but which includes one or more conductive contacts 196 located on an inner diameter of collet 195. Contacts 196 in one embodiment are constructed of corrosion-resistant metal, such as Berryllium-copper. When the proximal end of hub 193 is inserted into the distal end of handpiece 190, the contacts 194 of instrument 191 align and mate with contacts 196 of collet 194, so as to provide electrical energy to the electrode arrangement of housing element 192 without the need for a cable, such as cable 16. The cutting element and electrode arrangement of element 192 are controlled by integrated cutter control and RF control (ICC/RFC), or alternatively by separate (but interconnected) cutter control and RF control units, as discussed above.

Figure 18:
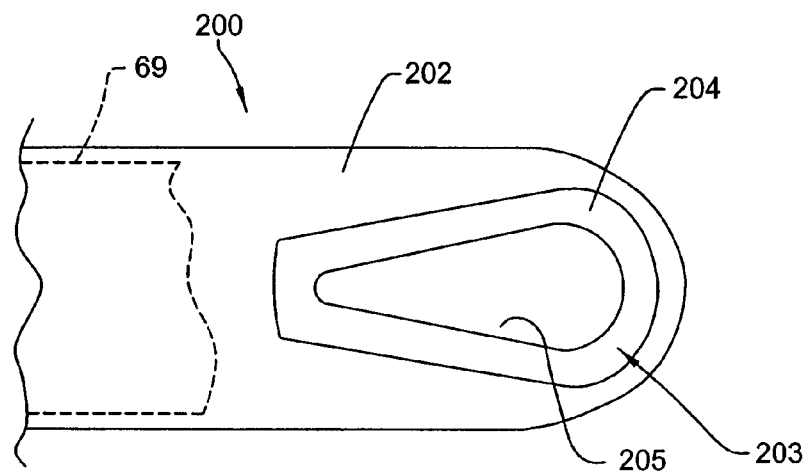
FIG. 18 is an enlarged and fragmentary top plan view of the distal end of a seventh embodiment of the combined electrosurgical and cutting instrument.
Figure 19:
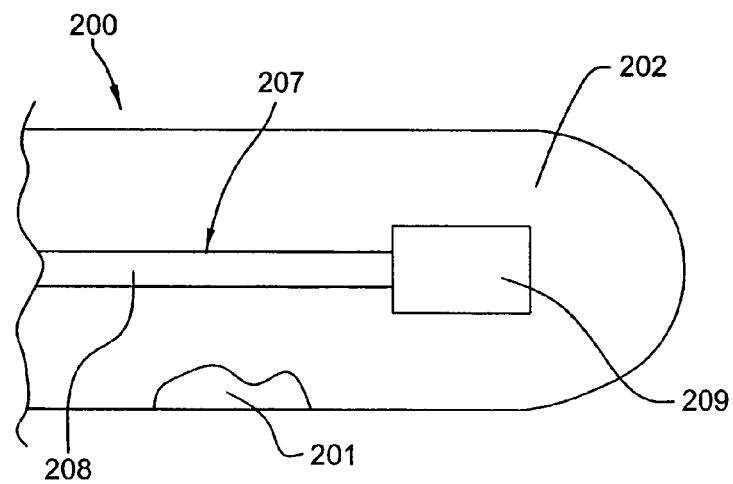
FIG. 19 is an enlarged and fragmentary bottom plan view of the combined electrosurgical and cutting instrument of FIG. 18.
Figure 20:
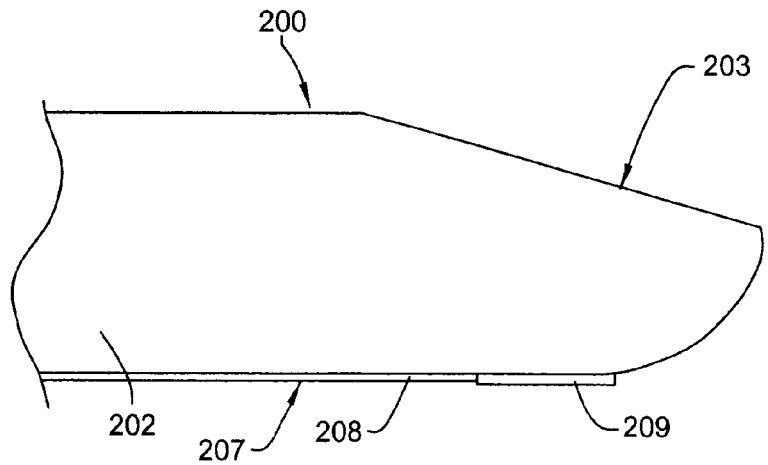
FIG. 20 is an enlarged and fragmentary side view of the combined electrosurgical and cutting instrument of FIG. 18.

FIGS. 18-20 illustrate a seventh embodiment of a combined electrosurgical tool and cutting instrument 200. The instrument 200 incorporates a static housing tube 201 which houses therein rotating drive shaft 69 of cutting element 15. Housing tube 201 in the illustrated embodiment is constructed of a conductive metal, such as stainless steel, and is coated, such as by powder-coating or other suitable coating method, on its exterior surface thereof with an insulating material 202. Housing tube 201 can then be cut, along with insulating layer 202, as described above to define a window 203 at the distal end of instrument 200. The cutting process exposes a ring-like or annular area 204 of housing tube 201 located inwardly of insulating layer 202. Area 204 defines a cutting edge 205 which cooperates with the cutting head 71 (not shown here) of cutting element 15 to sever tissue.

Housing tube 201 mounts thereon an electrode arrangement 207 which is secured to tube 201 over insulating layer 202 thereof. Electrode arrangement 207 in this embodiment is defined by an electrically-conductive wire or strip-like electrode element 208 which extends along the outer layer 202 of tube 201 and is covered with an insulating material. Electrode element 208 in one embodiment extends rearwardly into distal portion 46A (FIG. 2) of hub bore 46 and is electrically connected to cable 16. In another embodiment, electrode element 208 can be powered via contacts provided directly on the hub of instrument 200 as shown in FIG. 17. Electrode arrangement 207 additionally includes a generally flat, plate-like member 209 which is in electrical contact with electrode element 208, and which is un-insulated so as to define an active electrode. Active electrode 209 may be constructed of conductive metal, such as stainless steel or tungsten. Other suitable materials may be utilized.

In this embodiment, electrode element 208 and active electrode 209 are connected to one another by welding, or other suitable method, and are secured to the insulated layer 202 of housing tube 201 on the side of tube 201 which faces opposite or away from cutting window 203 via adhesive or other suitable fastening method.

In use, the active electrode 209 is utilized to deliver electrical energy to targeted patient tissue, and the exposed annular area 204 of housing tube 201 defines the return electrode, so as to define a bipolar instrument. In this regard, housing tube 201 can be electrically connected either to cable 16 (FIG. 1) or can be powered via contacts on the hub of instrument 200 as Figure in 17.

Figure 21:
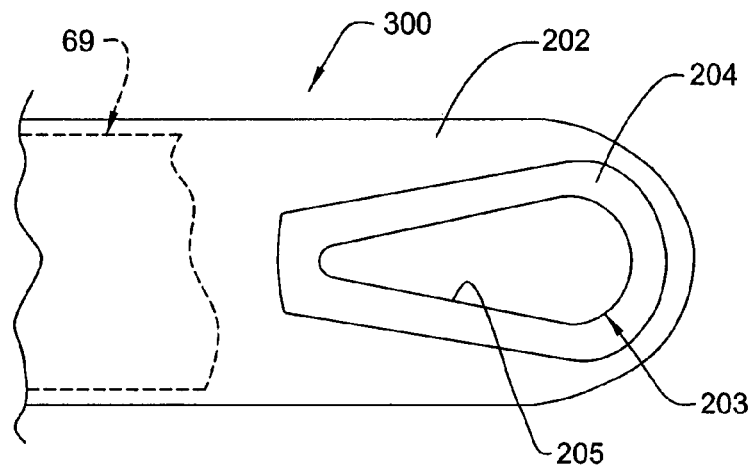
FIG. 21 is an enlarged and fragmentary top plan view of an eighth embodiment of the combined electrosurgical and cutting instrument.
Figure 22:
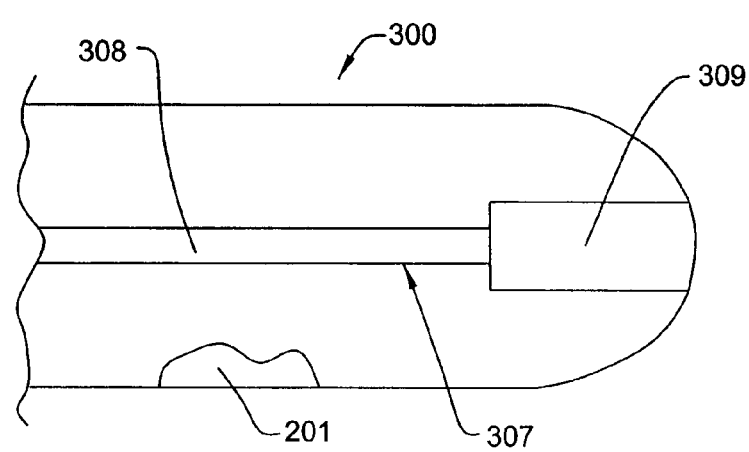
FIG. 22 is an enlarged and fragmentary bottom plan view of the combined electrosurgical and cutting instrument of FIG. 21.
Figure 23:
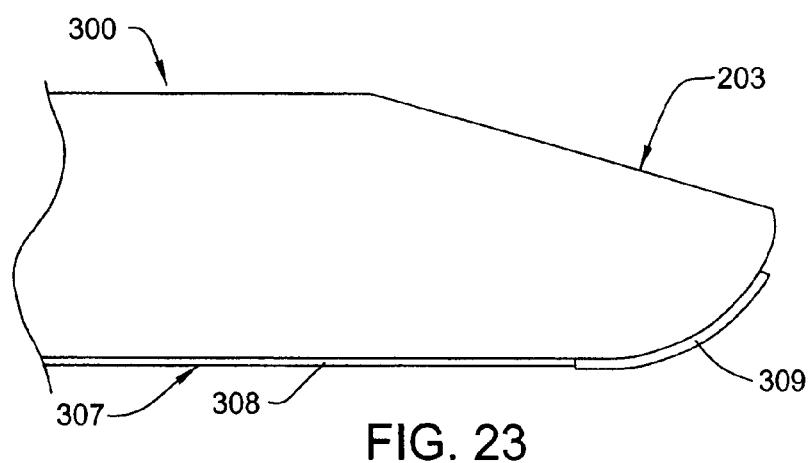
FIG. 23 is an enlarged and fragmentary side view of the combined electrosurgical and cutting instrument of FIG. 21.

FIGS. 21-23 illustrate an eighth embodiment of a combined electrosurgical tool and cutting instrument 300. The instrument 300 is similar to the embodiment shown in FIGS. 18-20, and thus the same or similar reference numbers will be utilized for the same or similar components.

The instrument 300 includes static and conductive housing tube 201 which houses therein rotating drive shaft 69, and which is coated with an insulating material 202. Housing tube 201 and layer 202 are cut so as to define window 203 at a distal end thereof, which exposes ring-like area 204 of tube 201 inwardly of insulating layer 202. Area 204 defines cutting edge 205 which cooperates with cutting head 71 to sever patient tissue. Housing tube 201 mounts thereon an electrode arrangement 307 which is secured to tube 201 over insulating layer 202 thereof. Electrode arrangement 307 in this embodiment is defined by an electrically-conductive wire or strip-like electrode element 308 which extends along the outer layer 202 of tube 201 and is covered with an insulating material. Electrode element 308 in one embodiment extends rearwardly into distal portion 46A (FIG. 2) of hub bore 46 for electrical connection to cable 16, or can be powered via contacts defined on the hub of instrument 300 as shown in FIG. 17. Electrode arrangement 307 additionally includes a thin conductive element 309 which is in electrical contact with electrode element 308, and which is un-insulated so as to define an active electrode. In this embodiment, similar to the embodiment of FIGS. 18-20, the electrode arrangement 307 is mounted on the side of housing tube 201 opposite the window 203. However, unlike active electrode 209, active electrode 309 conforms to the curvature of the distal end of housing tube 201 and projects a relatively short distance upwardly and over the distal end towards window 203. Active electrode 309 is constructed of conductive metal, such as stainless steel or tungsten. Other suitable materials may be utilized.

In this embodiment, electrode element 308 and active electrode 309 are connected to one another by welding, or other suitable method, and are secured to the insulated layer 202 of housing tube 201 on the side of same which faces opposite cutting window 203 via adhesive or other suitable method.

In use, the active electrode 309 is utilized to deliver electrical energy to the targeted patient tissue, and the exposed annular area 204 of housing tube 201 defines the return electrode, so as to define a bipolar instrument.

Figure 24:
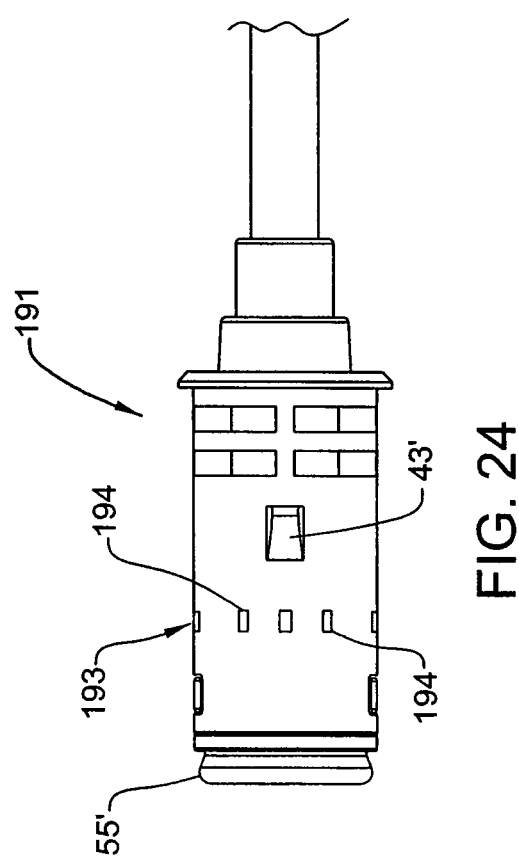
FIG. 24 is a more detailed fragmentary view of the combined electrosurgical and cutting instrument of FIG. 17.
Figure 25:
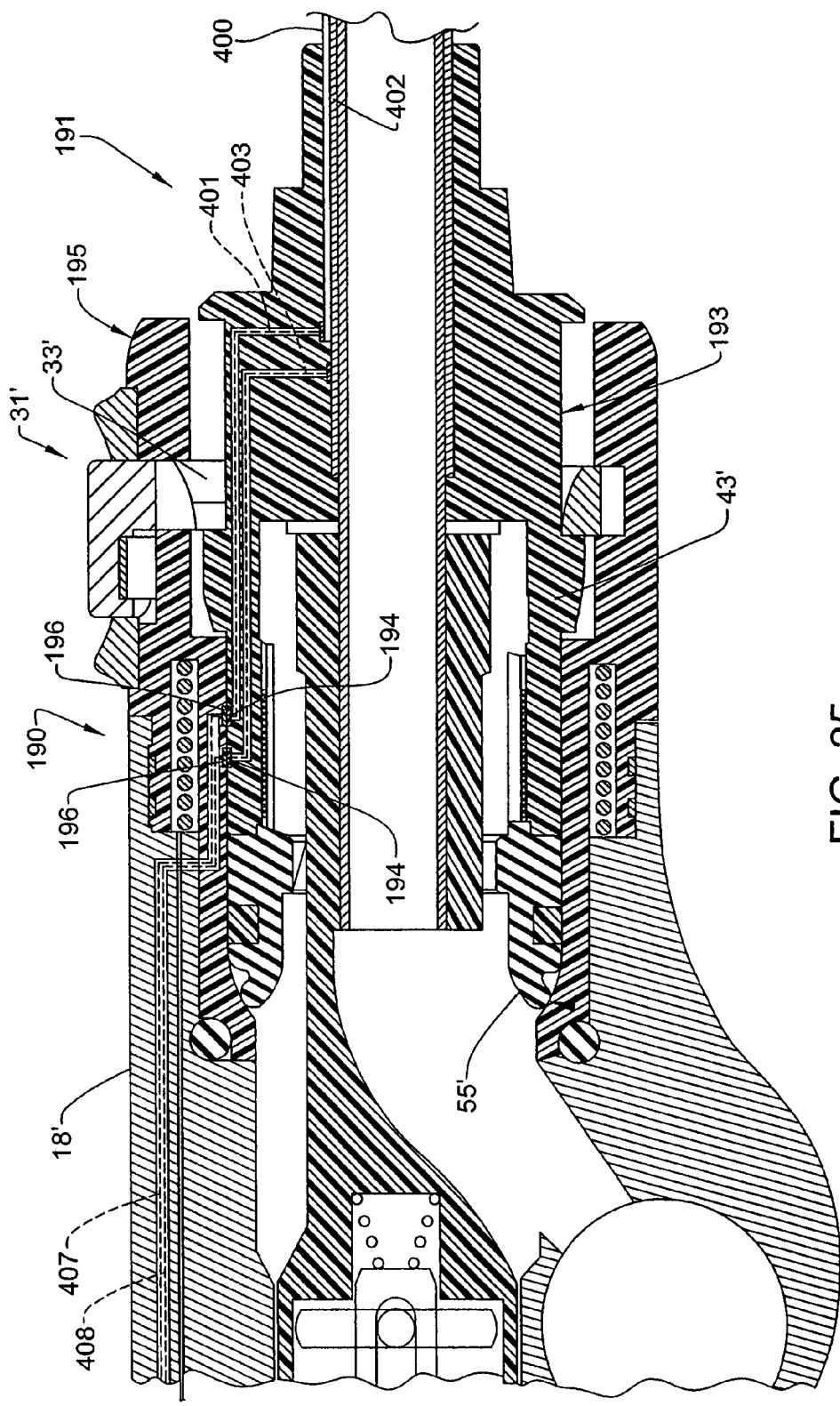
FIG. 25 is a more detailed enlarged, fragmentary longitudinal cross-sectional view of the surgical tool arrangement of FIG. 17.

FIGS. 24 and 25 illustrate more detailed views of the handpiece 190 and instrument 191 shown in FIG. 17. Handpiece 190 is similar to handpiece 11 shown in FIGS. 1 and 2, and the same reference numbers plus a "'" (prime) are accordingly utilized to identify the same or similar components. Likewise, electrosurgical and cutting instrument 191 is similar to instrument 12 as illustrated in FIG. 3, and the same reference numbers plus a "'" (prime) are thus utilized for the same or similar components.

Referring to FIGS. 24 and 25, instrument 191, as discussed above relative to FIG. 17, is provided with at least one, and here a plurality, of conductive spring contacts or blades 194 disposed about the outer circumference of hub 193. Contacts 194 are electrically connected to the active electrode 400 (which electrode 400 may represent any of the active electrode arrangements disclosed herein) via conductive elements such as wiring 401, and to the housing tube 402 (which housing tube 402 may represent any of housing tubes disclosed herein as being utilized as a return or common electrode) via conductive elements such as wiring 403. It will be appreciated that the wiring 401 and 403 which extends through hub 193 is shown diagrammatically only in FIG. 25. In this regard, some of the contacts 194 would be utilized for providing electrical energy to active electrode 400, while others of the contacts 194 would be utilized for returning the electrical energy from housing tube 402.

Turning now to handpiece 190, collet 195 is provided with at least one, and here a plurality, of conductive contacts 196 which in this embodiment are disposed about the inner circumference of collet 195. These contacts 196 are electrically connected to integrated cutter control and RF control (ICC/RFC) via cable 23 (FIG. 1) and wiring 407 and 408, which wiring 407, 408 is routed through collet 195 and housing 18' of handpiece 190 (wiring 407 and 408 being shown diagrammatically only in FIG. 25). It will be appreciated that contacts 196 are disposed on collet 195 in positions to allow same to mate with contacts 194 of instrument 191. Thus, some of the mating pairs of contacts 194 and 196 will be utilized as "active" contacts, while others of the mating pairs of contacts 194 and 196 will be utilized as "return" contacts.

In this regard, the contacts 194 and 196 are arranged on instrument 191 and collet 195, respectively, so that they will automatically align and mate with one another regardless of the rotational position of the instrument 191 relative to the collet 195 and handpiece 190. More specifically, the collet 195 which locks the instrument 191 to the handpiece 190 is similar to collet 32 described above, which collet 32 is configured to allow connection of instrument 191 in one of two positions located 180 degrees from one another. A detailed description of this feature of collet 32 is described in the Assignee's above-referenced '602 publication and will accordingly not be repeated herein. Further, it will be appreciated that the contacts 194 and 195 can be appropriately sealed so as to provide suitable sealing between the hub and handpiece electrical connection. Various sealing arrangements are discussed below.

Figure 26:
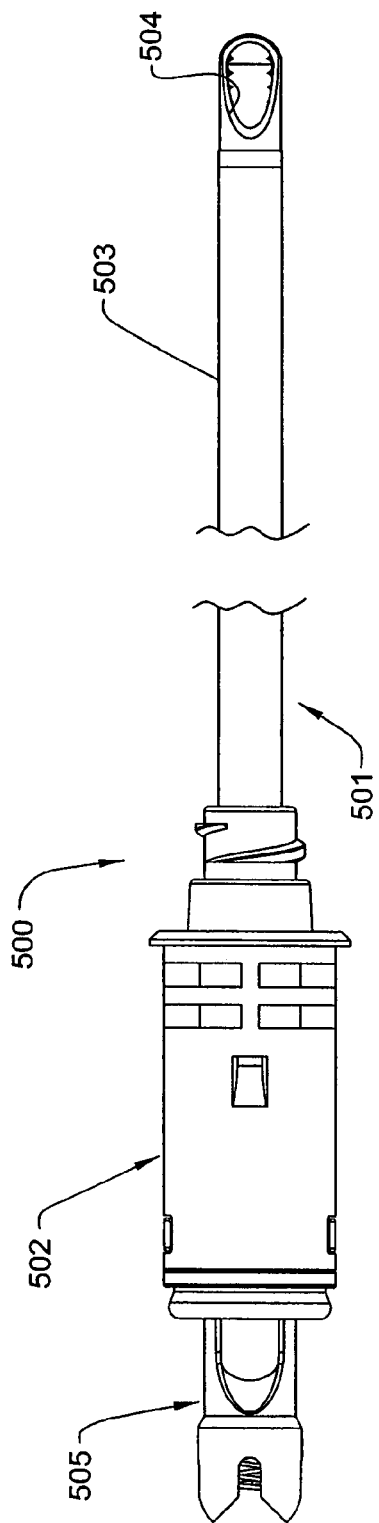
FIG. 26 is a fragmentary plan view of a surgical cutter or shaver instrument which can be utilized with the surgical tool arrangement shown in FIGS. 17 and 25.

It will be appreciated that the handpiece 190 illustrated in FIGS. 17 and 25 can be utilized with a variety of surgical instruments, each having one or multiple functions. More specifically, the handpiece 190 is powered by motor 20 (see FIG. 1), which can be used to drive a surgical cutter or shaver instrument 500 as illustrated in FIG. 26. Instrument 500 includes an outer housing assembly 501 having a hub 502 which is similar to hub 40 (FIG. 3), and an elongated outer tube 503 projecting outwardly from and connected to the hub 502. Outer tube 503 defines a cutting window 504 and an interior conduit in which a cutting element 505 is disposed. Cutting element is similar to cutting element 15 described above. When shaver instrument 500 is mounted to handpiece 190, output shaft of 21 of motor 20 drivingly engages the cutting element 505 and rotates same relative to outer tube 503 to sever patient tissue. Suction can also be drawn through cutting element 505 in order to remove fluid and other surgical debris from the surgical site. When utilizing this type of surgical instrument, the electrical contacts 196 of collet 195 of the handpiece 190 are not utilized, since this type of surgical instrument does not require electrical power to power any on board component.

Figure 27:
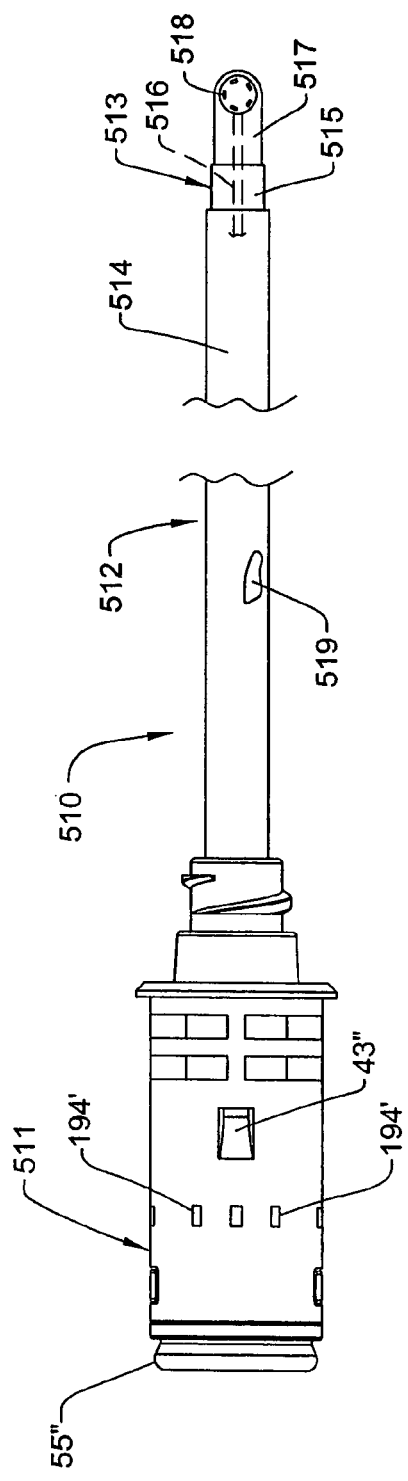
FIG. 27 is a fragmentary plan view of an electrosurgical instrument which can be utilized with the surgical tool arrangement shown in FIGS. 17 and 25.

Further, handpiece 190, with its integrated electrical contacts 196, is additionally usable with an electrosurgical instrument 510 as illustrated in FIG. 27. Electrosurgical instrument 510 includes a hub 511 which is substantially identical to hub 193 shown in FIG. 24, and the same references numbers plus a "'" (prime) are utilized to represent the same or similar components. Instrument 510 also includes a probe 512 which projects outwardly from hub 511. Probe 512 incorporates therein an inner conductive housing tube 513 which is covered along the majority of its length by an insulating tube or sheath 514. Part of housing tube 513 is exposed at its distal end so as to define a return electrode 515. An active electrode arrangement 516 is disposed within housing tube 513, and is mounted therein via an insulating cap or sleeve 517 which is seated in an open distal end of tube 513. In the illustrated embodiment, electrode arrangement 516 defines a plurality of active electrodes 518 at the distal end thereof. Electrode arrangement 516 and housing tube 513 are electrically connected to contacts 194'. The hollow interior of housing tube 513 defines a suction conduit 519, so that suction can be drawn through the probe 512 via handpiece 190.

When the electrosurgical instrument 510 is attached to handpiece 190, electrical contacts 194' mate with contacts 196 provided on the distal end of handpiece 190 so as to provide electrical power to electrode arrangement 516 and a return for housing tube 513 through the handpiece 190. Since instrument 510 does not include any component requiring the driving force of motor 20, this feature of handpiece 190 is not utilized with this instrument.

The handpiece 190, with its integrated electrical contacts 194 provided in the collet or coupling member 195, thus defines a universal handpiece which is usable with a variety of types of surgical instruments as described above, meaning that one handpiece is usable for a multitude of surgical procedures. The various surgical instruments or tools described herein are all adapted for use with the handpiece 190, and the appropriate instrument can thus be selected for the surgical procedure to be performed. These instruments may be disposable after one use. It is contemplated that other types of surgical instruments can be used with handpiece in addition to those described above, and the above are thus provided only as illustrative examples.

FIGS. 28 and 29 illustrate alternative electrical contact arrangements which cooperate between the hub and handpiece which may be utilized according to the present invention. The arrangement shown in FIG. 28 includes a hub 600 which incorporates therein a plurality of spring-loaded electrical contacts 601 on its outer circumference and generally near the distal end of the hub 600. An elastomeric seal 602 is placed around the hub 600 and serves to isolate the electrical contacts 601 from one another and seal the interface between the hub and handpiece. In this embodiment, the seal 602 is generally H-shaped. These contacts 601 are disposed to mate with correspondingly-positioned contacts 603 provided on the inner diameter of the handpiece collet 604.

With reference to FIG. 29, this arrangement includes a hub 610 which includes a plurality, and here three, of O-rings 611 which extend around the hub 610. Spring contacts 612 are provided on hub 610 between the respective pairs of adjacent seals or O-rings 611, which contacts 612 mate with conductive contacts, pads or tabs 613 provided on the inner surface of handpiece collet 614. The collet contacts 613 are offset from one another in the axial direction so as to allow the seals 611 provided on the hub 610 to seal between the contacts and to seal the electrical interface between the hub 610 and collet 614 from the outside environment.

Figure 30:
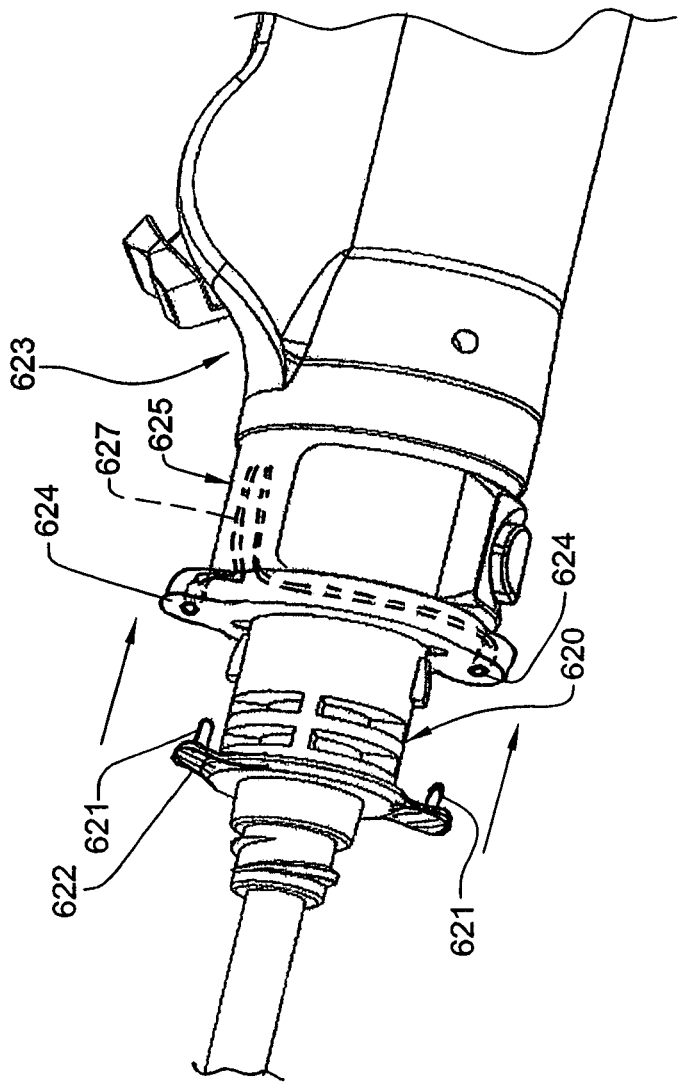
FIG. 30 is an enlarged and fragmentary view of an alternative hub and handpiece arrangement.

FIG. 30 illustrates an arrangement including a hub 620 which includes a pair of pin-type contacts 621 which are provided on opposite sides of the distal end of hub 620 via a mounting element 622 fixed to hub 620. The contacts 621 project proximally towards handpiece 623. Handpiece 623 includes a pair of correspondingly-positioned female contacts or receptacles 624 which are provided on a distal end of collet 625 of handpiece 623. Contacts 624 are electrically connected to the power source via wiring or conductive elements 627 (shown in dotted lines) through the handpiece 623. It will be appreciated that the pin-type contacts 621 may alternatively be provided on the handpiece 623, and the female contacts or receptacles 624 may then be provided on the hub 620. Further, small O-rings or seals (not shown here) can be provided around the pin-type contacts 621 on the side of mounting element 622 which faces proximally or towards handpiece 623, so as to seal the electrical interface between the hub 620 and handpiece 623.

Figure 31:
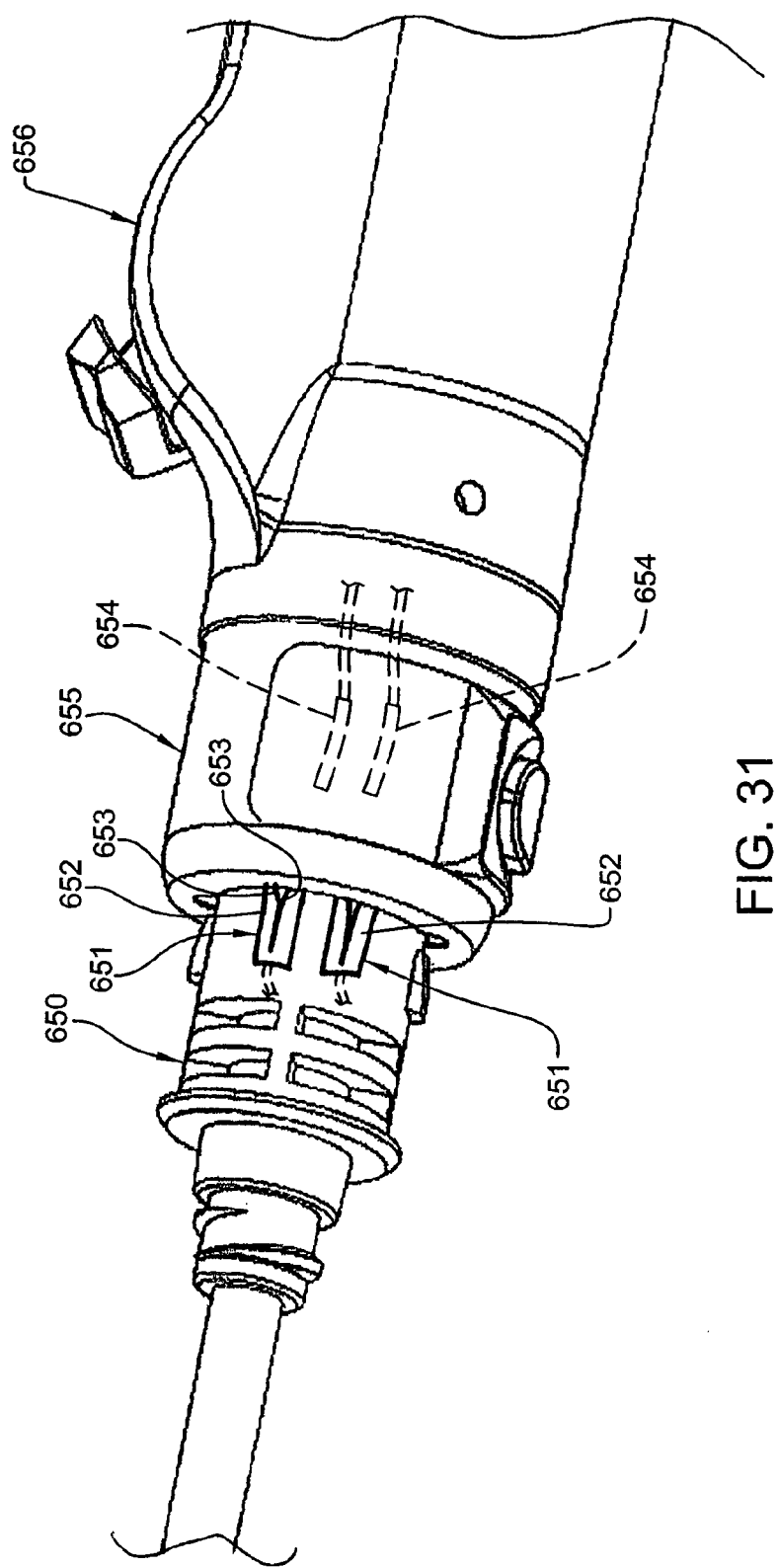
FIG. 31 is an enlarged and fragmentary view of a further alterative hub and handpiece arrangement.

FIG. 31 shows an arrangement including a hub 650 which includes a plurality of spring-type contacts 651 which are surrounded by respective seals 652, such as silicone seals. The contacts 651 are respectively embodied by a pair of conductive contact members 653 disposed in opposed relation with one another, which contact members 653 are surrounded by seal 652. The contacts 651 are disposed to mate with correspondingly-located contacts or blades 654 provided in the collet or coupling member 655 of handpiece 656. In this embodiment, two pairs of contacts 651 are provided in diametrically opposite positions on hub 650, and likewise two pairs of blades 654 are provided in diametrically opposite positions within collet 655 in positions corresponding to contacts 651. When the hub 650 is inserted into the collet 655, each contact blade 654 of collet 655 is axially inserted between a pair of opposed contact members 653 of a respective contact 651 of hub 650.

Figure 32:
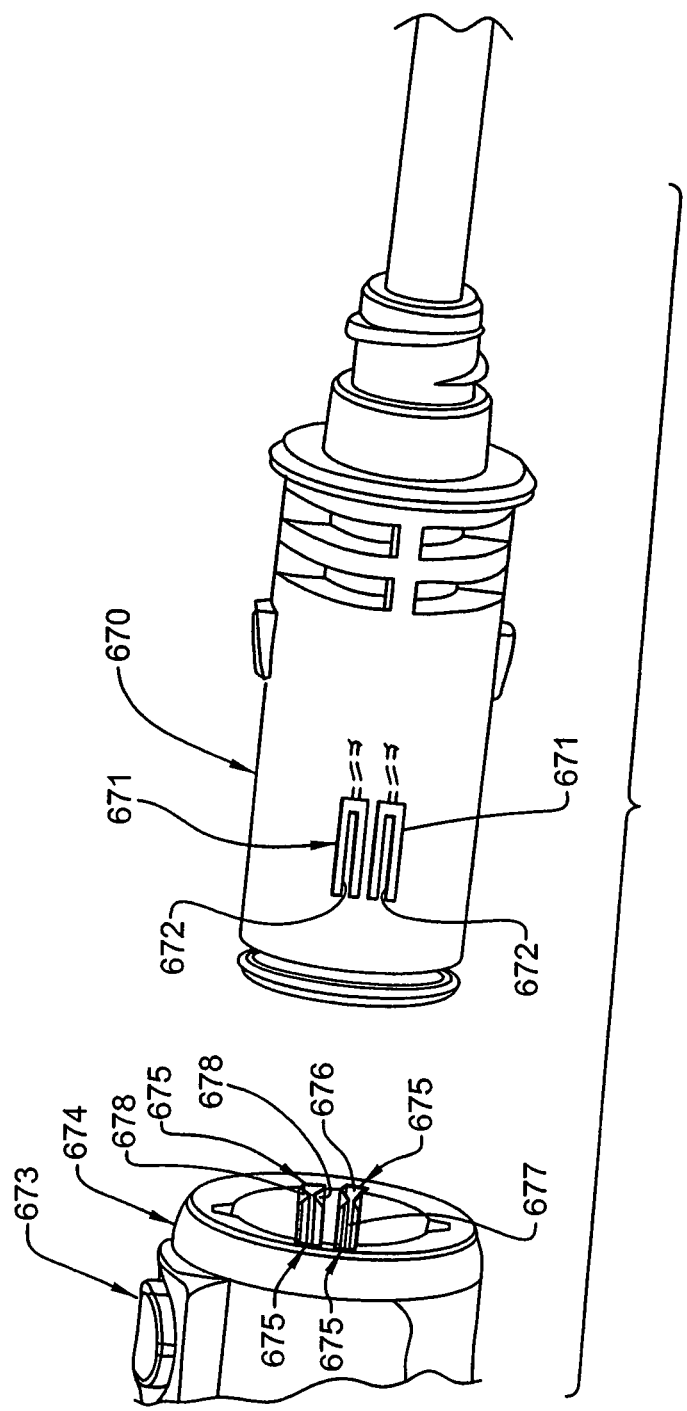
FIG. 32 is an enlarged, fragmentary exploded view of a further alternative hub and handpiece arrangement.

FIG. 32 illustrates an arrangement incorporating a hub 670 which mounts thereon a plurality of contacts 671. In this embodiment, contacts 671 are generally U-shaped so as to define a groove 672 therein, which groove 672 opens proximally towards handpiece 673. Two pairs of such contacts 671 are provided on hub 670 in diametrically opposite positions. The handpiece collet or coupling member 674 incorporates therein a plurality of contact elements 675 which include respective inwardly and distally-opening grooves 676. A blade or male contact 677 is provided in each groove 676, and a pair of seals 678 are provided in facing relation with one another on opposite sides of each groove 676 adjacent the distal end thereof. Two pairs of contacts 675 are provided within collet 674 on diametrically opposite sides thereof in locations corresponding to the locations of the contacts 671 of hub 670. Upon insertion of hub 670 into collet 673, each blade 677 is inserted into a respective groove 672 of a corresponding contact 671, and the seals 678 serve to seal the electrical interface between the hub 670 and handpiece 673.

The above hub and handpiece arrangements which permit electrical interface between these two components are configured so as to allow easy axial insertion of the hub and associated surgical instrument into the handpiece, and also provide sealing at this interface. It will be appreciated that other types of electrical interfaces may be used, provided that same provide a sturdy and secure electrical connection between the two components.

Although a particular preferred embodiment of the invention is disclosed in detail for illustrative purposes, it will be recognized that variations or modifications of the disclosed apparatus, including the rearrangement of parts, lie within the scope of the present invention.

What is claimed is:

1. A surgical tool arrangement comprising a handpiece including a housing defining a hollow interior, a proximal end and a distal end spaced therefrom, a motor disposed in said interior and including an output member, a coupling member disposed on said distal end of said housing and including thereon an electrical contact member connected to an electrical power source by an electrical conductor extending through said interior in a proximal direction away from said coupling member, said arrangement further including a surgical instrument for detachable connection to said handpiece, said surgical instrument including a hub configured for interlocking engagement with said coupling member to attach said surgical instrument to said handpiece, a drive element operatively connected to and driven by said output member of said motor, and an electrode arrangement for electrically treating patient tissue, said hub of said surgical instrument mounting thereon an electrical contact member electrically connected to said electrode arrangement, said drive element being supported on said surgical instrument for movement relative to said contact member of said hub when said drive element is driven by said output member, said contact member of said coupling member and said contact member of said surgical instrument being disposed to make electrically-conducting contact with one another when said surgical instrument is attached to said handpiece to provide electrical power to said electrode arrangement.

2. The arrangement of claim 1, wherein said hub of said surgical instrument is a first hub, said surgical instrument including an outer stationary housing assembly including said first hub which defines thereon a mounting arrangement configured for interlocking engagement with said coupling member of said handpiece, said outer housing assembly including an outer cannula connected to said first hub and defining a window at a distal end thereof, said electrode arrangement being mounted on said outer cannula and defining an electrode disposed adjacent said window for electrically treating patient tissue, said surgical instrument further including a cutting assembly movably disposed within said outer housing assembly and including a second hub configured for being coupled to and driven by said output member of said motor, said cutting assembly including a movable mechanical cutting member including said drive element, said drive element being connected to said second hub and having a cutting head at a distal end thereof, said cutting head being disposed adjacent said window to sever patient tissue.

3. The arrangement of claim 2, wherein said handpiece defines a suction passage in communication with a suction source, said drive element is tubular and defines a suction conduit therein, said drive element defining an opening disposed adjacent said cutting head in communication with said suction conduit, and said suction conduit communicates with said suction passage of said handpiece so as to permit suction of fluid and/or surgical debris from a surgical site through said opening.

4. The arrangement of claim 1, wherein said coupling member is tubular and has an outer circumferential surface and an inner circumferential surface, said contact member of said coupling member being disposed adjacent said inner circumferential surface, and said contact member of said surgical instrument being disposed adjacent an outer surface of said hub.

5. The arrangement of claim 1, wherein said handpiece defines a longitudinal axis, said contact member of said coupling member comprising one of a male connector and a female connector, said connector being oriented generally parallel to, but spaced radially from, the longitudinal axis, and said connector directly contactingly engaging said contact member of said surgical instrument when installed on said handpiece in a direction substantially parallel to the longitudinal axis.

6. The arrangement of claim 1, wherein said electrode arrangement of said surgical instrument is bipolar and includes an active electrode and a return electrode and said contact member of said surgical instrument is a first contact member, said hub of said surgical instrument mounting thereon a second electrical contact member, said first contact member of said surgical instrument being electrically connected to said active electrode and said second contact member being electrically connected to said return electrode, said contact member of said coupling member of said handpiece is a first contact member and said electrical conductor is a first electrical conductor, said coupling member including a second contact member connected to an electrical power source by a second electrical conductor extending through said interior in a proximal direction away from said coupling member, said first contact member of said coupling member being disposed to mate with said first contact member of said surgical instrument associated with said active electrode and said second contact member of said coupling member being disposed to mate with said second contact member of said surgical instrument associated with said return electrode, and a seal is disposed on either said hub of said surgical instrument or said coupling member of said handpiece to electrically isolate the mating pairs of contact members of said surgical instrument and said coupling member from one another.

7. The arrangement of claim 1, wherein said contact member of said hub of said surgical instrument is spring-loaded so as to automatically engage with said contact member of said coupling member upon insertion of said hub of said surgical instrument into said coupling member.

8. The arrangement of claim 1, wherein said coupling member defines a central axis, and said contact members are disposed for engagement with one another in a direction substantially parallel to the central axis upon insertion of said hub of said surgical instrument into said coupling member.

9. The arrangement of claim 1, wherein said drive element has a longitudinal axis and is operatively coupled to and rotatably driven by said output member of said motor about the axis.

10. The arrangement of claim 9, wherein said drive element includes a cutting element at a distal end thereof configured for severing patient tissue during rotation of said drive element.

11. The arrangement of claim 1, wherein said drive element has a longitudinal axis and is operatively coupled to and rotatably driven by said output member of said motor about the axis, said contact member of said coupling member and said contact member of said surgical instrument being disposed to make substantially non-rotatable and electrically-conducting contact with one another during rotation of said drive element.

12. A surgical tool arrangement comprising a handpiece including a housing defining a hollow interior, a proximal end and a distal end spaced therefrom, a motor disposed in said interior, a driving member operatively connected to said motor, and a coupling member disposed on said distal end of said housing and including thereon an electrical contact member connected to an electrical power source by an electrical conductor extending through said interior in a proximal direction away from said coupling member, said arrangement further including a surgical instrument for detachable connection to said handpiece, said surgical instrument including a tissue cutting member operatively connected to said driving member such that actuation of said motor causes movement of said tissue cutting member to sever patient tissue at a surgical site, a hub and an electrode arrangement for electrically treating patient tissue, said hub of said surgical instrument including an electrical contact member electrically connected to said electrode arrangement, said contact member of said coupling member and said contact member of said surgical instrument being disposed in electrically-conducting contact with one another when said surgical instrument is attached to said handpiece, said tissue cutting member being movable relative to said contact member of said surgical instrument when said tissue cutting member is moved by said driving member.

13. The arrangement of claim 12, wherein said hub defines a proximal end of said surgical instrument, said hub defining thereon a mounting arrangement configured for interlocking engagement with said coupling member of said handpiece, and said surgical instrument including a housing member connected to said hub of said surgical instrument and mounting thereon said electrode arrangement at a distal end thereof for electrically treating patient tissue.

14. The arrangement of claim 13, wherein said handpiece defines a suction passage in communication with a suction source, said housing member of said surgical instrument is tubular and defines a suction conduit therein, said housing member defining an opening disposed adjacent said distal end of said housing member in communication with said suction conduit, and said suction conduit communicates with said suction passage of said handpiece so as to permit suction of fluid and/or surgical debris from a surgical site through said opening.

15. The arrangement of claim 12, wherein said hub of said surgical instrument is a first hub, said surgical instrument including an outer stationary housing assembly including said first hub which defines thereon a mounting arrangement configured for interlocking engagement with said coupling member of said handpiece, said outer housing assembly including an outer cannula connected to said first hub and defining a window at a distal end thereof, said electrode arrangement being mounted on said outer cannula and defining an electrode disposed adjacent said window for electrically treating patient tissue, said surgical instrument further including a cutting assembly movably disposed within said outer housing assembly and including said tissue cutting member, a second hub configured for being coupled to and driven by said driving member of said motor, said tissue cutting member including an elongate drive shaft connected to said second hub and having a cutting head at a distal end thereof, said cutting head being disposed adjacent said window to sever patient tissue.

16. The arrangement of claim 15, wherein said handpiece defines a suction passage in communication with a suction source, said drive shaft is tubular and defines a suction conduit therein, said drive shaft defining an opening disposed adjacent said cutting head in communication with said suction conduit, and said suction conduit communicates with said suction passage of said handpiece so as to permit suction of fluid and/or surgical debris from a surgical site through said opening.

17. The arrangement of claim 12, wherein said coupling member is tubular and has an outer circumferential surface and an inner circumferential surface, said contact member of said coupling member being disposed adjacent said inner circumferential surface, and said contact member of said surgical instrument being disposed adjacent an outer surface of said hub.

18. The arrangement of claim 12, wherein said handpiece defines a longitudinal axis, said contact member of said coupling member comprising one of a male connector and a female connector, said connector being oriented generally parallel to, but spaced radially from, the longitudinal axis, and said connector directly contactingly engaging said contact member of said surgical instrument upon attachment of said surgical instrument to said handpiece in a direction generally parallel to the longitudinal axis.

19. The arrangement of claim 12, wherein said electrode arrangement of said surgical instrument is bipolar and includes an active electrode and a return electrode and said contact member of said surgical instrument is a first contact member, said hub of said surgical instrument includes a second electrical contact member, said first contact member of said surgical instrument being electrically connected to said active electrode and said second contact member being electrically connected to said return electrode, said contact member of said coupling member of said handpiece is a first contact member and said electrical conductor is a first electrical conductor, said coupling member including a second contact member connected to an electrical power source by a second electrical conductor extending through said interior in a proximal direction away from said coupling member, said first contact member of said coupling member being disposed to mate with said first contact member of said surgical instrument associated with said active electrode and said second contact member of said coupling member being disposed to mate with said second contact member of said surgical instrument associated with said return electrode, and a seal is disposed on either said hub of said surgical instrument or said coupling member of said handpiece to electrically isolate the mating pairs of contact members of said surgical instrument and said coupling member from one another.

20. The arrangement of claim 12, wherein said contact member of said hub of said surgical instrument is spring-loaded so as to automatically engage with said contact member of said coupling member upon insertion of said hub of said surgical instrument into said coupling member.

21. The arrangement of claim 12, wherein said tissue cutting member defines an axis, said hub of said surgical instrument is configured for cooperative engagement with said coupling member to attach said surgical instrument to said handpiece, said hub substantially non-rotatably mounting thereon said contact member, said contact member of said surgical instrument being disposed in substantially non-rotatable contact with said contact member of said coupling member during rotation of said tissue cutting element about the axis.

* * * * *